United States Patent

Lerouge et al.

Patent Number: 5,549,718
Date of Patent: Aug. 27, 1996

[54] SUBSTANCE WITH LIPO-OLIGOSACCHARIDE STRUCTURE CAPABLE OF ACTING AS PLANT-SPECIFIC SYMBIOTIC SIGNALS, PROCESSES FOR PRODUCING THEM AND THEIR APPLICATIONS

[75] Inventors: Patrice Lerouge; Philippe Roche, both of Toulouse; Catherine Faucher; Fabienne Maillet, both of Ramonville Saint Agne; Jean Denarie, Castanet-Tolosan; Jean-Claude Promé, Pechbusque; Georges Truchet, Castanet-Tolosan, all of France

[73] Assignees: Centre National de la Recherche Scientifique (C.N.R.S.), Paris; Institut National de la Recherche Agronomique (I.N.R.A.), Paris Cedex, both of France

[21] Appl. No.: 315,491

[22] Filed: Sep. 30, 1994

Related U.S. Application Data

[63] Continuation of Ser. No. 214,676, Mar. 21, 1994, abandoned, which is a continuation of Ser. No. 930,662, filed as PCT/FR91/00283 on Apr. 5, 1991, abandoned.

[30] Foreign Application Priority Data

Apr. 6, 1990 [FR] France .................. 90 04764

[51] Int. Cl.$^6$ .................. A01C 1/06; A01H 3/04; C12P 19/04; C12R 1/41
[52] U.S. Cl. .................. 47/57.6; 47/58; 536/17.2; 536/22.1; 536/123.1; 435/84; 435/172.3; 435/252.2; 435/878; 514/54
[58] Field of Search .................. 536/17.2, 22.1, 536/123.1; 435/84, 252.2, 878, 172.3; 514/54; 47/58, 57.6

[56] References Cited

FOREIGN PATENT DOCUMENTS

| 3735365 | 4/1988 | Germany . |
| 8706796 | 11/1987 | WIPO . |

OTHER PUBLICATIONS

Chemical Abstracts, vol. 102, No. 3, 21 Jan. 1985, (Columbus, Ohio, US), M. Abe et al.: "Stimulation of Clover root hair infection by lectin-binding oligosacharides from the capsular and extracellular polyscharies of Rhizobium trifolii", p. 416, abstract 21445p, & J. Bacteriol. 1984, 160(2), 517–20.

Chemical Abstract, vol. 110 No. 25, 19 Jun. 89, (Columbus, Ohio, US), p. 689, abstract 232023c, & JP, A. 63255294 (Ihara Chemical Industry Co., Ltd.) 21 Oct. 1988.
Nature, vol. 344, 19 Apr. 90, P. Lerouge et al.: "Symbiotic host-specificity of Rhizobium meliloti is determined by a suphated and acylated glucosamine oligosaccharide signal", pp. 781–784.
Journal of Bacteriology, vol. 172, No. 2, Feb. 1990, pp. 901–911, Mary A. Honma, et al., "Rhizobium Meliloti nod Genes Mediate Host-Specific Activation of nodABC".
Journal of Bacteriology, vol. 168, No. 3, Dec. 1986, pp. 1075–1086, Frederic Debelle, et al., "Assignment of Symbiotic Developmental Phenotypes To Common And Specific Modulation (nod) Genetic Loci of Rhizobium Meliloti".
The EMBO Journal, vol. 2, No. 6, pp. 947–952, J. Allan Downie, et al., "Cloning Of The Symbiotic Region Of Rhizobium Leguminosarum: The Modulation Genes Are Between The Nitrogenase Genes And a nifA-Like Gene" (1983).
Kosslak et al. 1987. PNAS USA 84: 7428–7432.
Truchet et al. 1985. J. Bacteriol. 164:1200–1210.
Faucher et al. 1988, J. Bacteriol. 170:5489–5499.

*Primary Examiner*—David T. Fox
*Attorney, Agent, or Firm*—Oblon, Spivak, McClelland, Maier & Neustadt, P.C.

[57] ABSTRACT

An essentially pure substance has a structure of a Nod factor or one of its analogues. The Nod factor is characterized by the fact that its biosynthesis is controlled by at least one nodulation gene (nodA,B,C) common to the Rhizobiaceae, in particular to the genera Rhizobium, Bradyrhizobium, Sinorhizobium and Azorhizobium. This substance consists of a lipo-oligosaccharide which is not a derivative of the exopolysaccharides and which has the general formula (I). In formula (I), the Nod factor of which it has the structure is a plant-specific symbiotic signal and is capable of enhancing the capacity of the bacteria of infect the host plant with which it is associated and/or of accelerating the formation of nodules on the host plant with which it is associated and/or of inducing the transcription of symbiotic genes of the leguminoseae. Applications to the treatment of plants and as an active therapeutic agent in humans and animals. G stands for a hexosamine variously substituted, for example by an acetyl group on the nitrogen, a sulphate group, an acetyl group and/or an ether group on oxygen $R_1$, $R_2$, $R_3$, $R_5$, $R_6$, $R_7$, which may be identical or different, stand for H, $CH_3CO-$, $C_xH_yCO-$ where X is a whole number between 0 and 17 and Y is a whole number between 1 and 35, or any other acyl group, for example a carbamyl groups, $R_4$ stands for a saturated or mono-, di or tri-unsaturated aliphatic chain containing at least 12 carbon atoms and n is a whole number between 1 and 4.

11 Claims, 18 Drawing Sheets

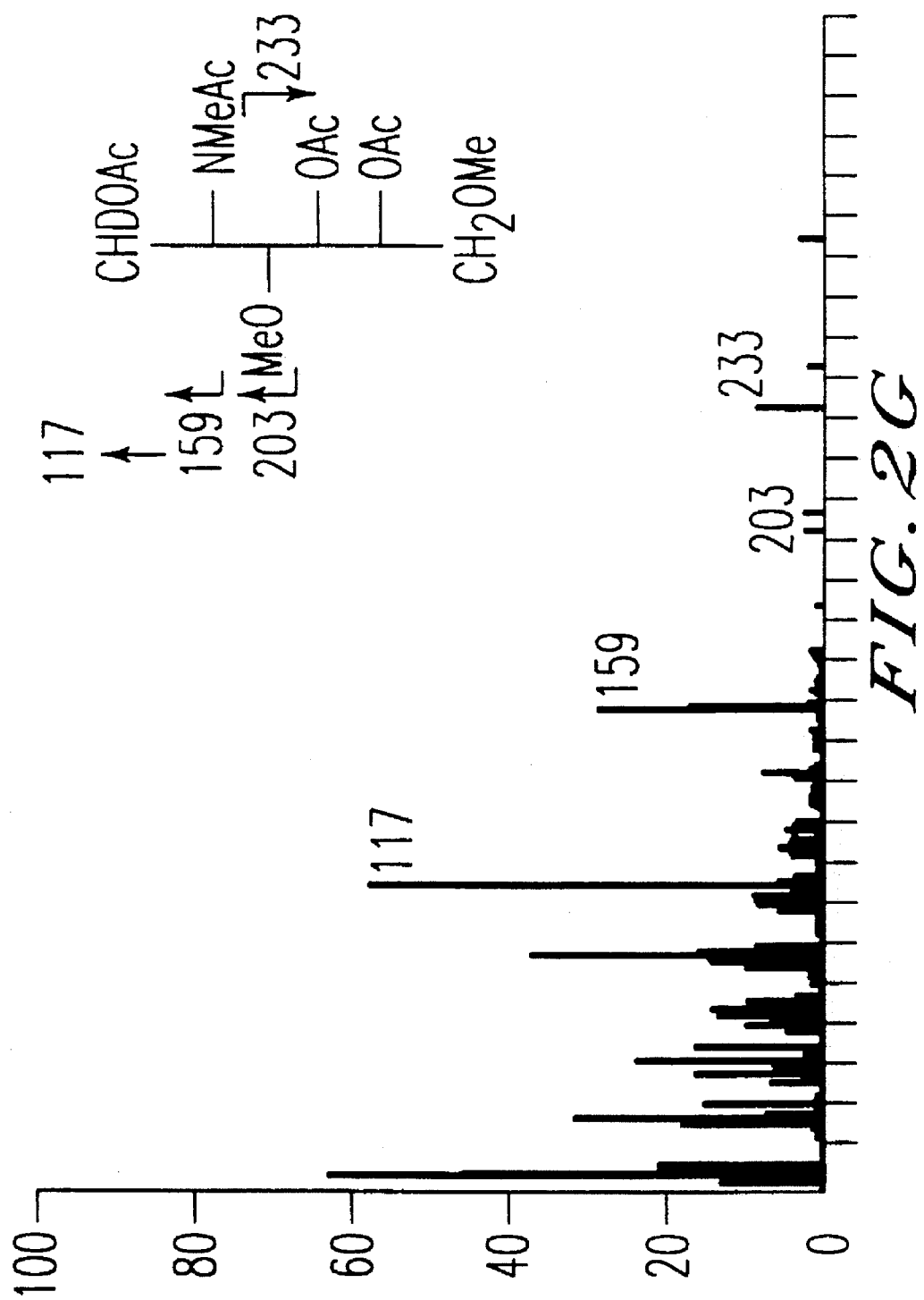

M/Z

SUBSTANCE WITH LIPO-OLIGOSACCHARIDE STRUCTURE CAPABLE OF ACTING AS PLANT-SPECIFIC SYMBIOTIC SIGNALS, PROCESSES FOR PRODUCING THEM AND THEIR APPLICATIONS

This application is a Continuation of application Ser. No. 08/214,676, filed on Mar. 21, 1994, now abandoned, which is a Continuation of application Ser. No. 07/930,662, filed as PCT/FR91/00283, on Apr. 5, 1991, now abandoned.

BACKGROUND OF THE INVENTION

1. Field of the Invention

The present invention relates to substances of lipo-oligosaccharide structure which are capable of forming plant-specific symbiotic signals, to processes for producing these substances and to their applications.

2. Discussion of the Background

As it is known, plants require for their growth a source of combined nitrogen such as ammonia or nitrate. The fixing of nitrogen, by chemical or biological reduction of atmospheric nitrogen ($N_2$) to ammonia ($NH_3$), therefore plays a vital role in agricultural production.

As it is also known, symbiotic microorganisms can promote the growth and development of plants through biological fixation of nitrogen.

Rhizobiaceae are Gram negative soil bacteria which generally fix nitrogen in symbiotic association with plants: the establishment of such symbiosis with nitrogen-fixing bacteria allows numerous plant species to grow in soils with low assimilable nitrogen levels. By virtue of photosynthesis, the plant partner provides the bacteria with the energy required for reducing molecular nitrogen to ammonia. In return, the ammonia fixed by the microsymbiont is provided to the host plant which incorporates it into its nitrogen metabolism. The symbiotic association which is established between nitrogen-fixing bacteria such as Rhizobiaceae and plants of the Leguminoseae family is the most important from an ecological and agronomic point of view. This association leads to the formation of nodosities or nodules mainly on the roots of the host plants. Inside these nodosities, the bacteria reduce atmospheric nitrogen to ammonia by means of the nitrogenase enzymatic complex.

The symbiosis between nitrogen-fixing bacteria of the Rhizobiaceae family (Rhizobium, Bradyrhizobium, Sinorhizobium and Azorhizobium genera) and plants of the Leguminoseae family therefore play a very important role in temporate and tropical agriculture. Oil- and protein-rich plants such as soybean and groundnut, fodder plants such as lucerne and clover, protein-rich plants such as peas and field bean, food plants such as beans, peas, lentils and chickpeas, green manures such as Sesbania and the like. By virtue of these symbioses, the cultivation of Leguminoseae is often less costly in nitrogenous fertilizer than the cultivation of plants belonging to other families. In this respect, it should be noted that the massive use of nitrogenous fertilisers has certain disadvantages. Firstly, the synthesis, transportation and application of fertilizers is costly in fossil energy, and this has several consequences: at the farming level it increases the production hosts of the farmers, and at the environmental level it contributes to the greenhouse effect by increasing the $CO_2$ content. Moreover, an ill thought-out or excessive application of nitrogenous fertilizers causes pollution of fresh waters with eutrophication of the surface waters and an increase in the nitrate content of the ground water table. These various reasons militate in favor of an increased use of biological fixation of nitrogen.

Given the very damaging consequences of the excessive use of nitrogenous fertilizers, it is therefore necessary to increase the contribution of the biological fixation of nitrogen by plants and in particular by the cultivated species which play an important role in human and animal nutrition. The most acceptable solution both from the ecological and economical point of view is to improve the Rhizobiaceae-Leguminoseae symbiosis.

It has been proposed to carry out this improvement by providing Rhizobiaceae (in particular Rhizobium or *Bradyrhizobium*) at the time of sowing, either by coating the seeds or by means of granules mixed with the seeds or by means of cultivation in liquid medium. These bacteria supplies are however effective only in the relatively rare cases where the appropriate symbiotic bacteria are naturally absent or are not very abundant in the soils. In the opposite cases, that is to say in soils already containing these bacteria, it is practically impossible to impose a strain which is deliberately introduced, due to competition with the indigenous bacteria present in the soils, which, even if they are not necessarily effective for fixing nitrogen, constitute nevertheless a limiting factor for introducing selected bacteria.

It has also been proposed to enhance the Rhizobium-Leguminoseae symbiosis by treating the plants with an exopolysaccharide derived from bacteria of the Rhizobium genus or with an oligosaccharide containing one or more units of such an exopolysaccharide (EPS)—cf. the PCT International Application published under the No. WO 87/06796 filed on behalf of THE AUSTRALIAN NATIONAL UNIVERSITY and mentioning as inventors:. B. G. ROLFE, S. P. DJORDJEVIC, J. W. REDMOND and M. BATLEY. However, this EPS is a product encoded by non-symbiotic genes. In fact, the biosynthesis of these exopoly-saccharides is not under the direct control of the nod genes which control infection and nodulation. These exopolysaccharides are synthesized by Rhizobium strains whose plasmid pSym has been cured, which plasmid carries most of the symbiotic genes and in particular the nod genes.

The genes involved in the nodule-formation process have been localized and several common and specific nodulation genes (nod genes) have been identified and characterized (see Long, S. R., Cell, 1989, 56, 203–214). Whereas the nodA,B,C genes are nodulation genes which are common to the various species of symbiotic Rhizobiaceae, specific nod genes exist which determine the host spectrum and which therefore vary in the various species, and regulatory genes of the nodD type which control the expression of the entire nod genes.

The common genes nodA,B,C have been identified in the four bacterial genera which are capable of establishing a nitrogen-fixing symbiosis with the Leguminoseae: Rhizobium, Bradyrhizobium, Sinorhizobium and Azorhizobium. For the Rhizobium genus, the nucleotide sequeuence of these genes has been obtained in *R. meliloti* (Török et al., Nucleic Acids Res., 1984, 12, 9509–9522; Jacobs et al., *J. Bacteriol.*, 1985, 162, 469–476; Egelhoff et al., DNA, 1985, 4, 241–242). *R leguminosarum* (Rossen et al., Nucl. Acids Res., 1984, 12, 9497–9508 ), *R. trifolii* (Schofield et al., Nucl. Acids Res:., 1986, 14, 2891–2903).

For *Bradyrhizobium sp.* ( Scott, Nucl. Acids Res., 1986, 14, 2905–2919).

For *Azorhizobium caulinodans* (Goethals et al., Mol. Gon. Genet., 1989, 219, 289–298).

A team of researchers comprising several of the inventors of the present invention have shown that in *Rhizobium meliloti*, the common genes nodA,B,C induce, conjointly with the specific genes nodH and nodQ, the production of the host-specific extracellular Nod signals present in the culture supernatants of these bacteria: cf. FAUCHER et al., *J. BACTERIOL* (1988), 172, 5489–5429 and FAUCHER et al., Molec. Plant-Microbe Interact. (1989), 2, 291–300, among others. Furthermore, the latter of these two publications gives an account of the fractionation of the sterile supernatant by ultrafiltration thus making it possible to reveal the presence of two Nod factors with an apparent molecular mass of less than 5,000 Da.

The specificity of infection and nodulation is determined in *R. meliloti* at two levels, namely:—the nodD genes activate the expression of other nod operons depending on the presence of specific signals produced by the plants (Gyorgypal et al., Molec. Gen. Genet., 1988, 212, 85–92) and, —specific genes such as nodH and nodQ determine, when they are activated, the production of bacterial extracellular signals (Nod factors) which make it possible to recognize and stimulate a host leguminous plant such as lucerne (Faucher et al., *J. Bacteriol*, 1988, 172, 5489–5499; Faucher et al., *Molec. Plant-Microbe Interact.*, 1989, 2, 291–300 ). However, the chemical structure of the bacterial signals was not known.

SUMMARY OF THE INVENTION

The aim of the present invention is therefore to define the chemical structure of symbiotic Nod signals and to provide substances possessing such a chemical structure and also to provide processes for producing substances which are capable of acting as such symbiotic Nod signals and to propose applications of these substances for the treatment of organisms belonging both to the plant and animal kingdoms (including man).

The subject of the present invention is an essentially pure substance possessing the structure of a Nod factor or of one of its analogs, which Nod factor is characterized by the fact that its biosynthesis is under the control of at least one nodulation gene (nodA,B,C) common to the Rhizobiaceae, in particular to the Rhizobium, Bradyrhizobium, Sinorhizobium and Azorhizobium genera, which substance is characterized in that it consists of a lipo-oligosaccharide not derived from exopolysaccharides.

BRIEF DESCRIPTION OF THE DRAWINGS

FIGS. 2E–2G are vapor phase chromatograms of the compound described in Example B.2.4.

FIG. 4C is negative FAB ionization mass spectrum.

Figure 1A:
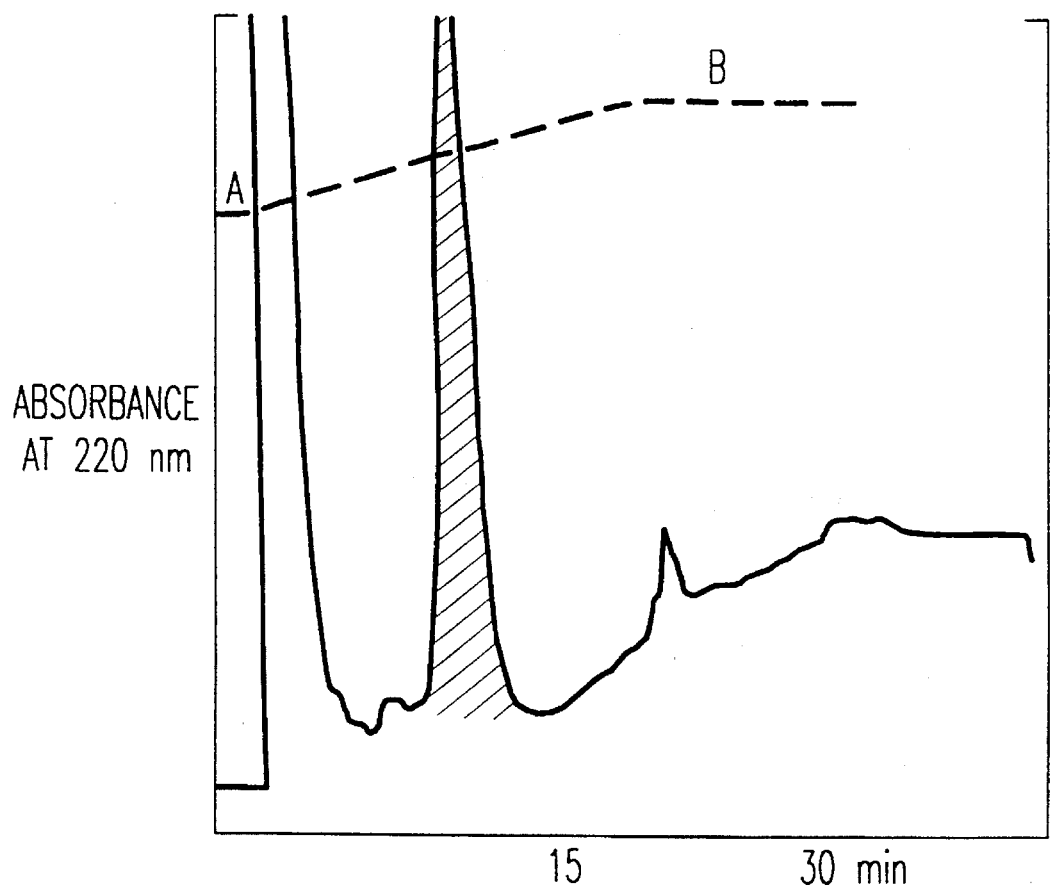
FIG. 1A is a reverse-phase HPLC chromatogram of the compound extracted from *Rhizobium meliloti* as described in Example B.1.2.
Figure 1B:
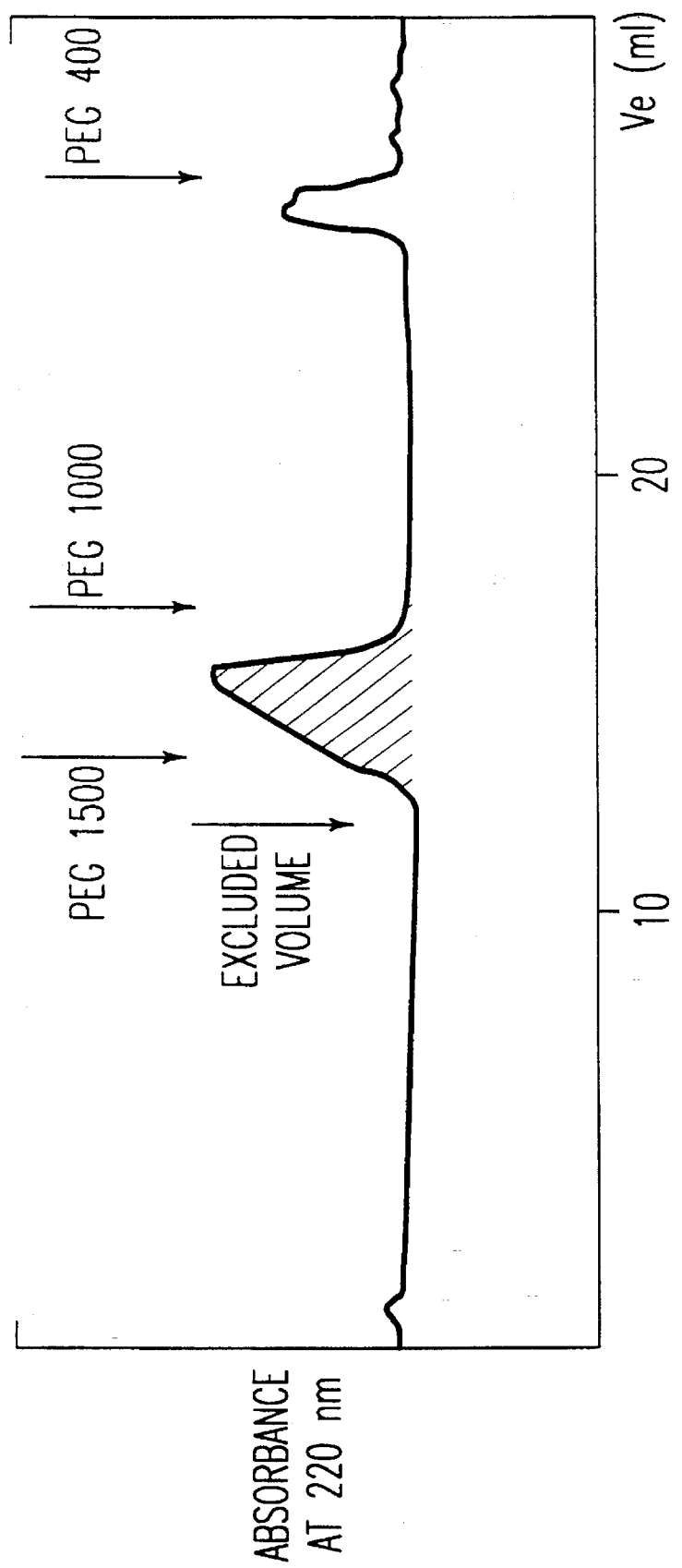
FIG. 1B is a gel permeation chromatogram of the compound described in Example B.1.3.
Figure 1C:
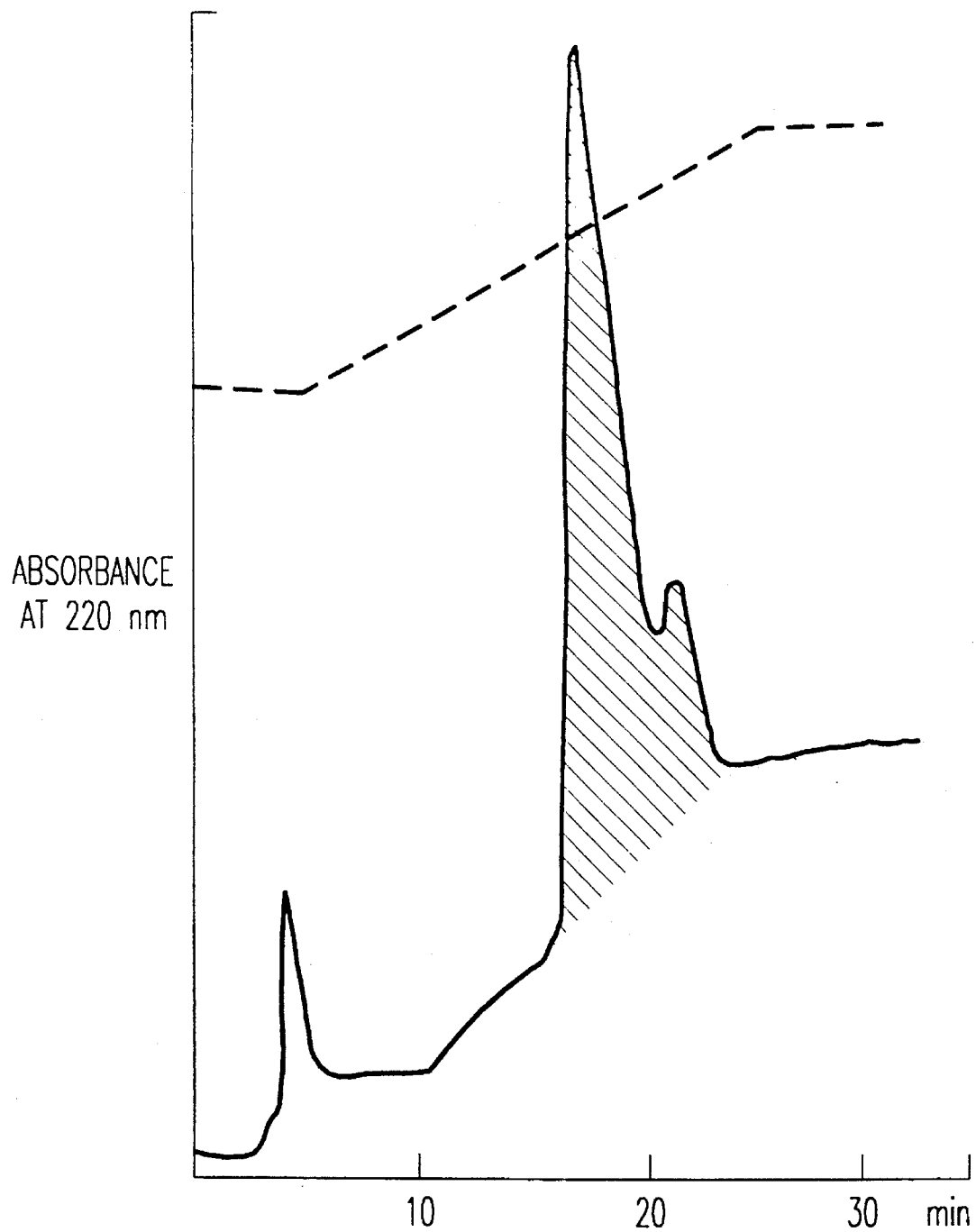
FIG. 1C is an ion-exchange chromatogram of the compound described in Example B.1.4.
Figure 1D:
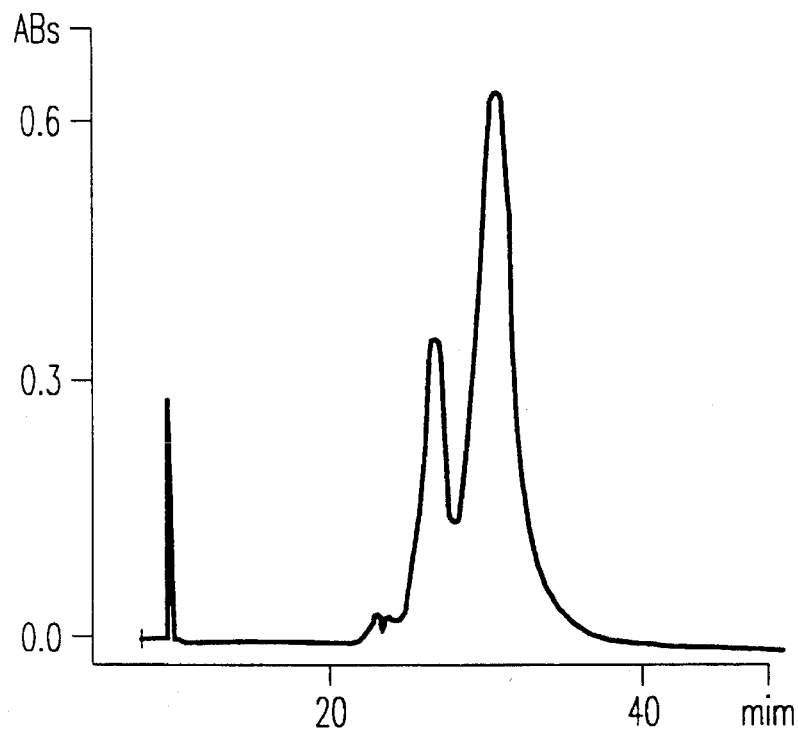
FIGS. 1D–1E are reverse phase HPLC chromatograms of the compound described in Example B.1.5.
Figure 1E:
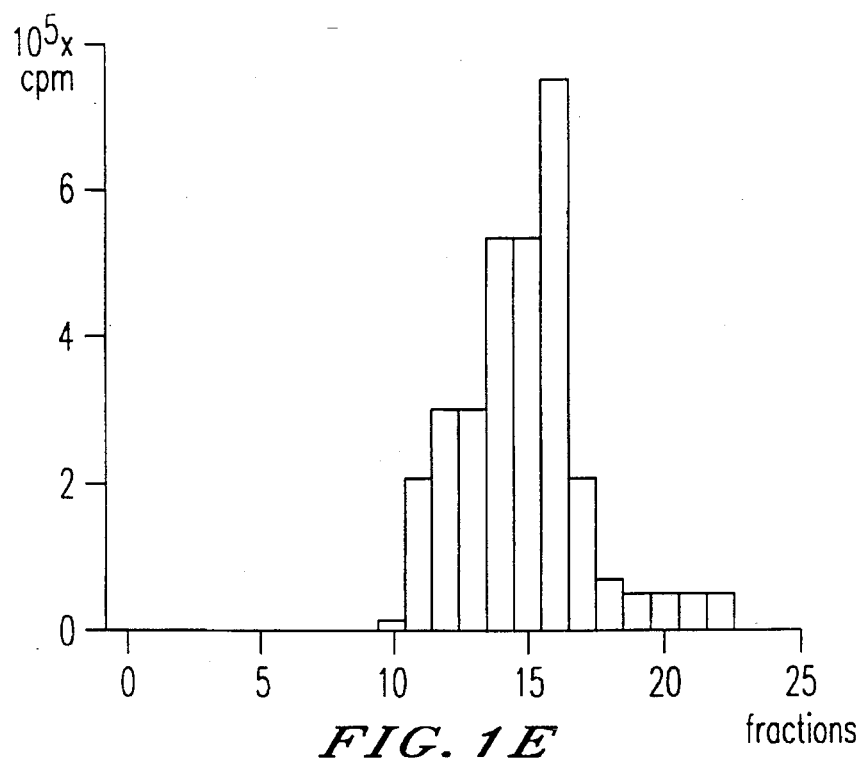
Figure 2A:
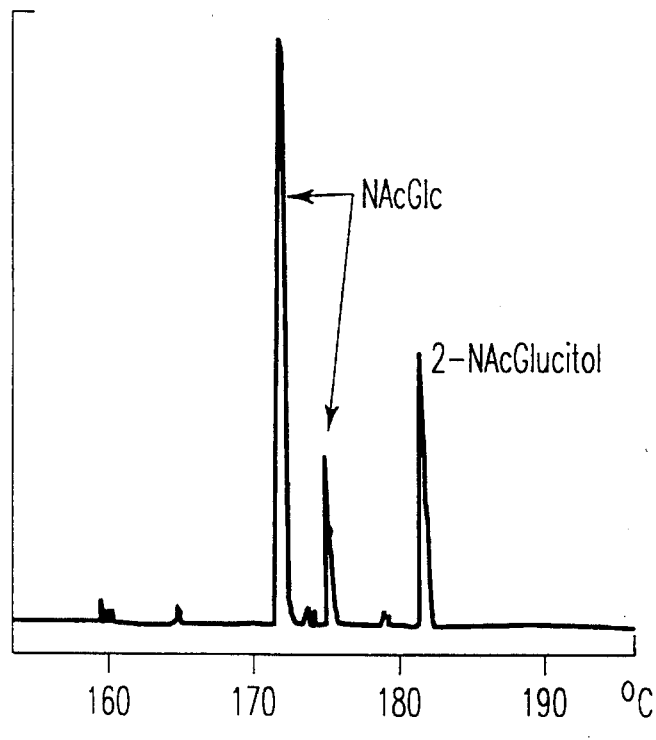
FIG. 2A is a vapor phase chromatogram of the reduced compound described in Example B.2.1.
Figure 2B:
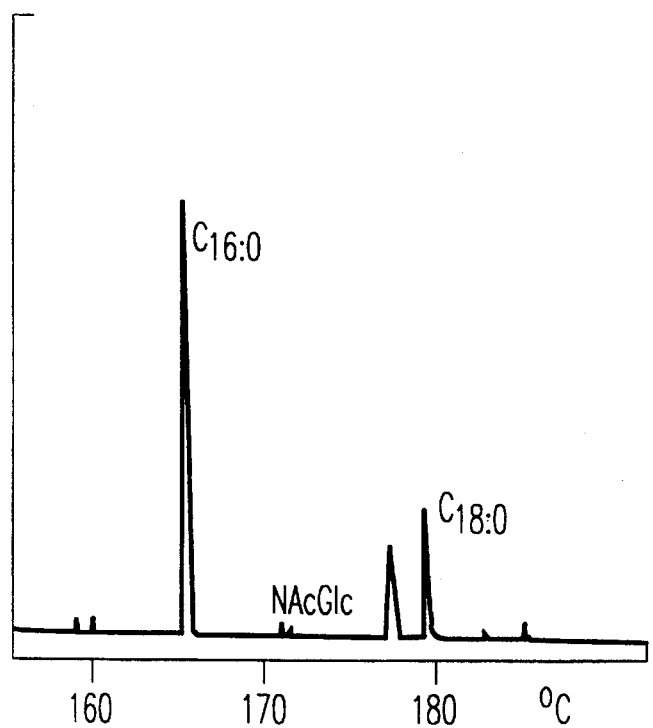
FIG. 2B is a vapor phase chromatogram of the hydrogenated compound described in Example B.2.1.
Figure 2C:
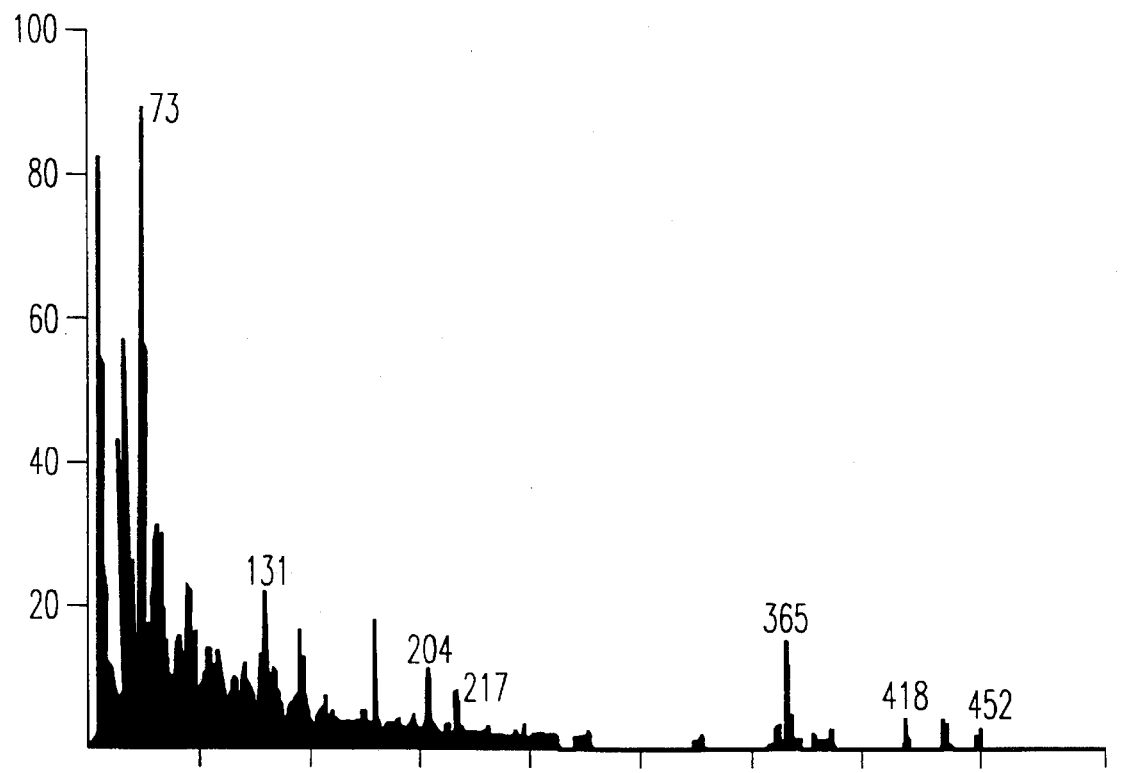
FIG. 2C is an electron impact mass spectra of the reduced compound described in Example B.2.1.
Figure 2C:
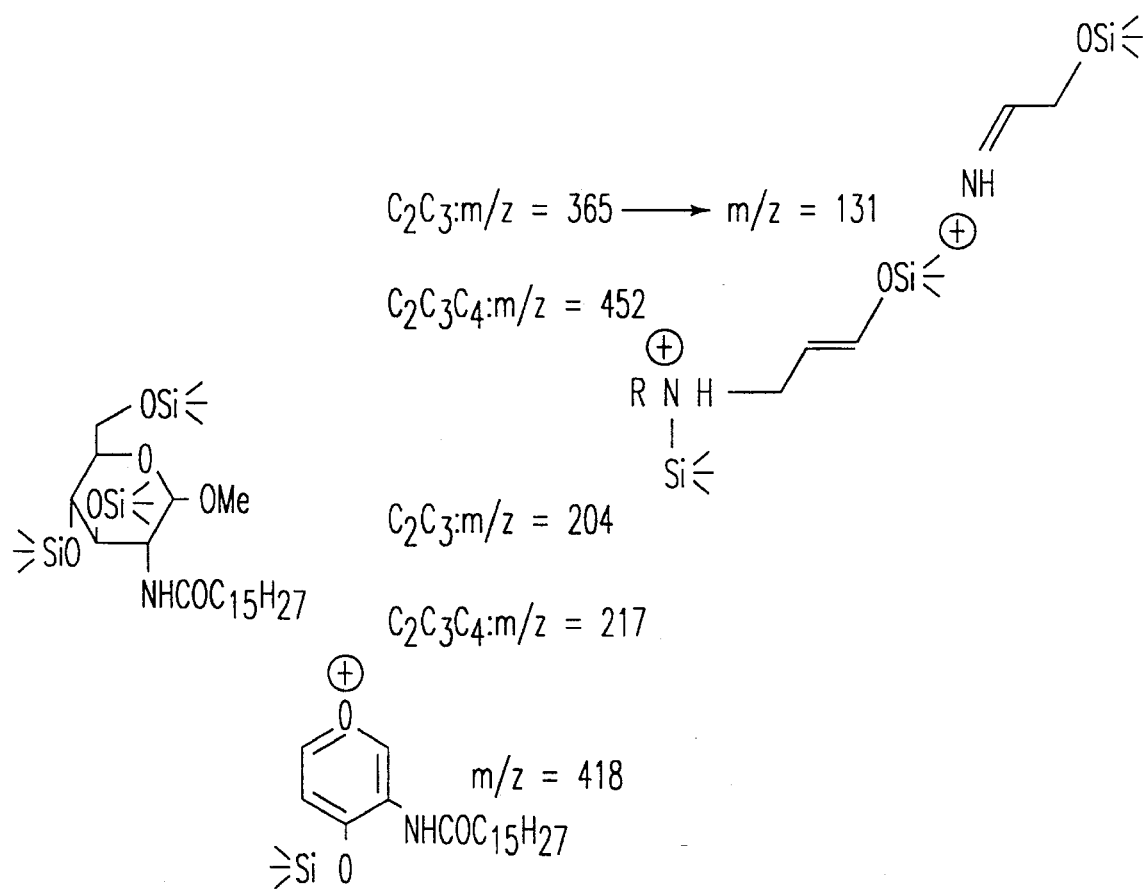
Figure 2D:
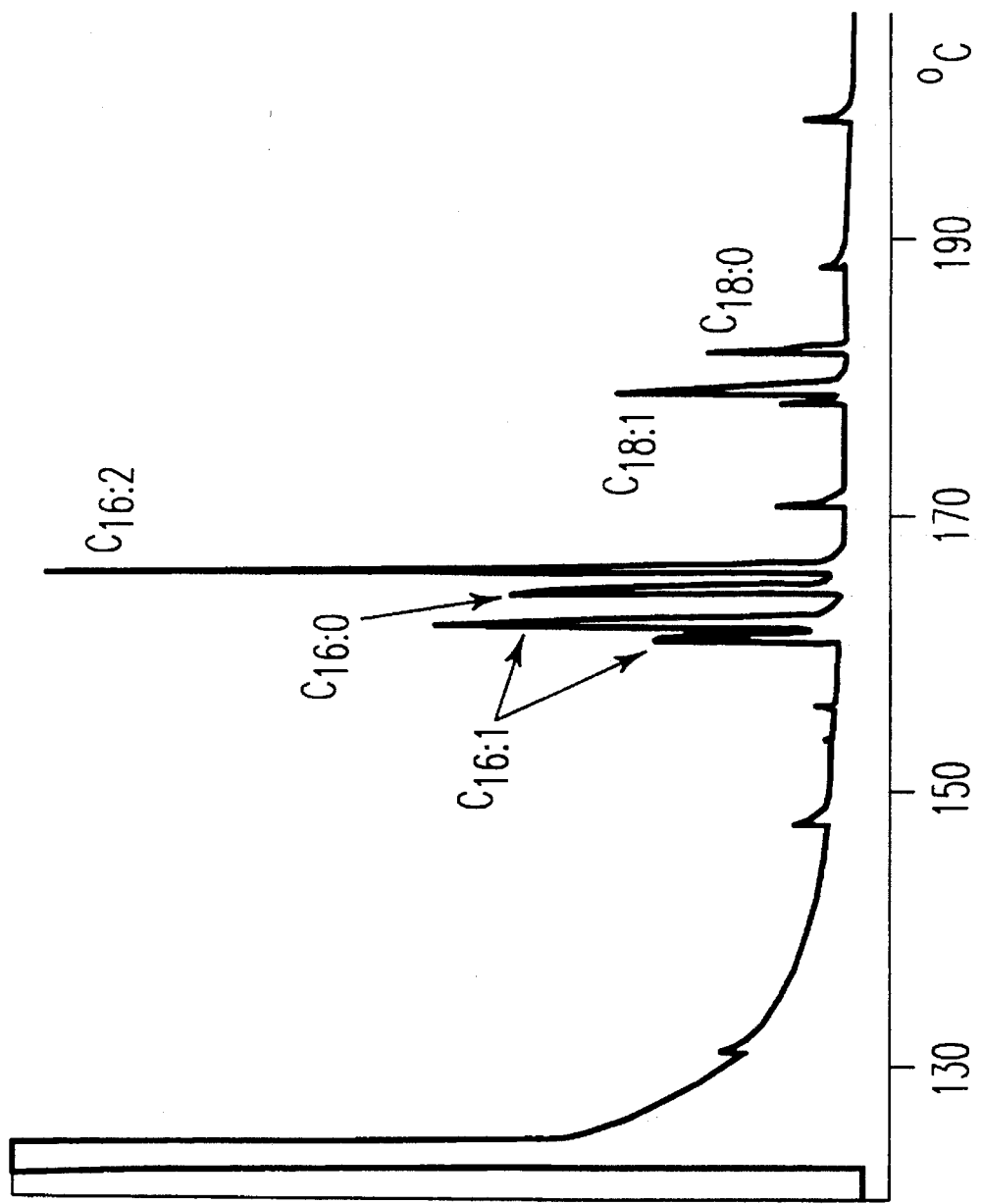
FIG. 2D is a vapor phase chromatogram of the compound described in Example B.2.2.
Figure 2E:
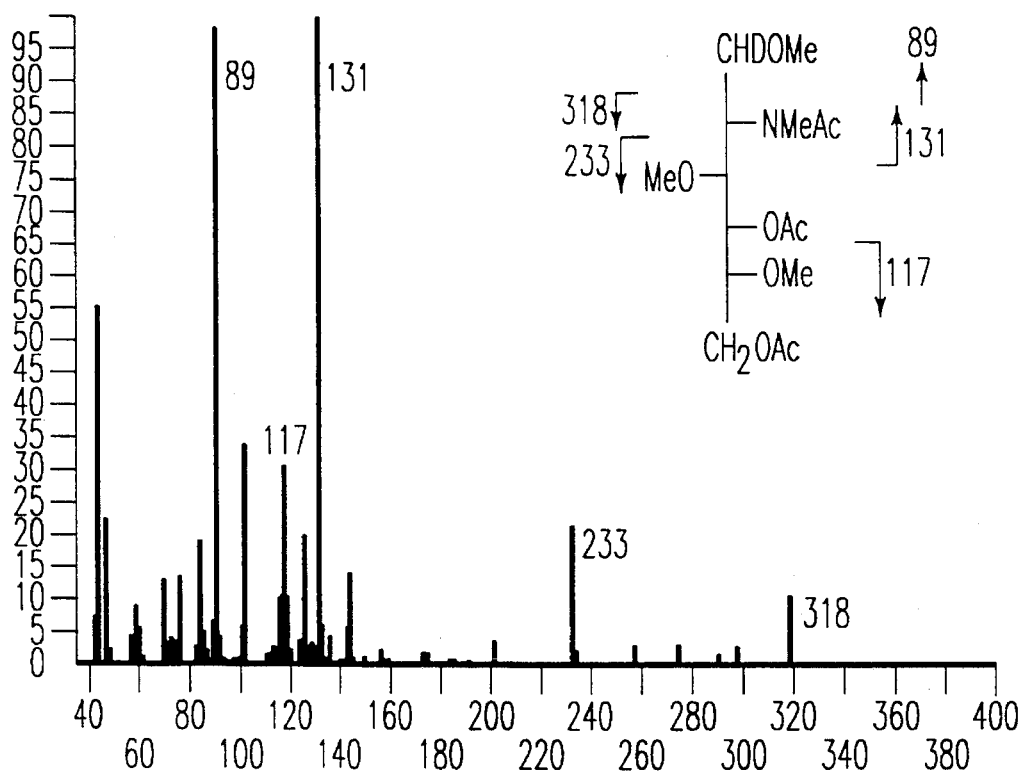
Figure 2F:
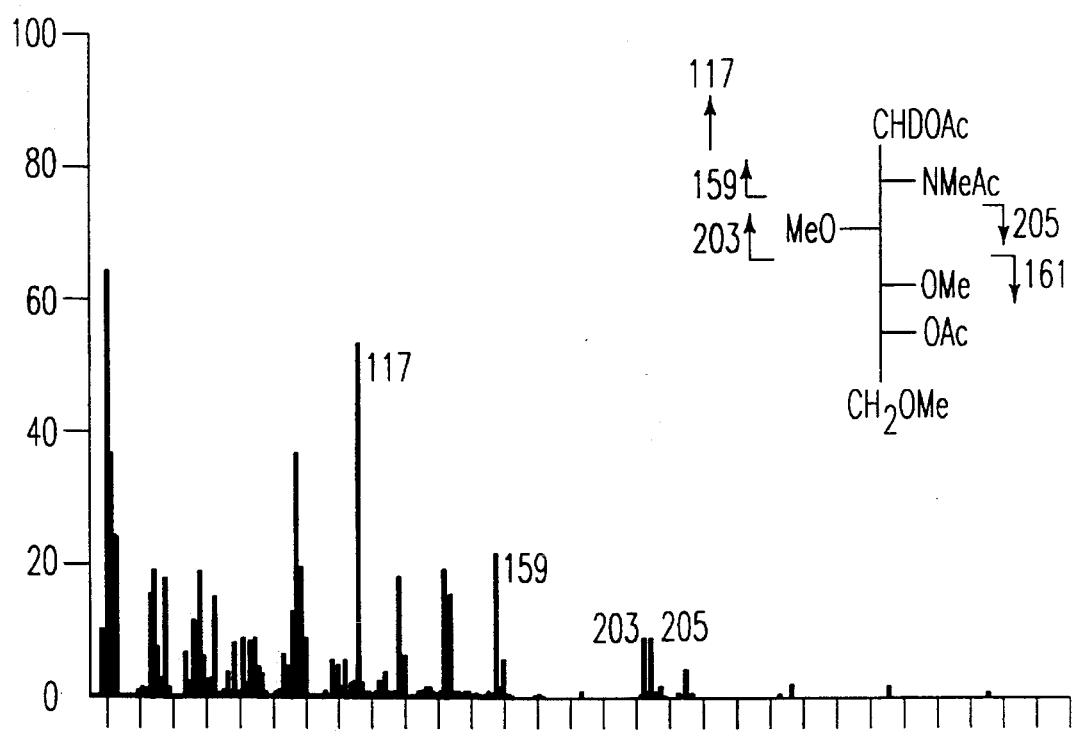

Within the context of the present invention, "Nod factor" is understood to mean a signal molecule produced under the direct control of nod genes, by means of which signal the symbiotic bacteria are capable of infecting plants and inducing the formation of nodosities.

According to an advantageous embodiment of the said essentially pure substance, the Nod factor whose structure it possesses is characterized in that it is a plant-specific symbiotic signal and is capable of enhancing the capacity of the bacteria to infect the host plant with which it is associated and/or of accelerating the formation of nodules on the host plant with which it is associated and/or of inducing the transcription of the symbiotic genes of Leguminoseae.

According to another advantageous embodiment of the said essentially pure substance conforming to the invention, the Nod factor whose structure it possesses has the structural properties of a lectin ligand.

The subject of the present invention is also a lipo-oligosaccharide substance characterized in that it is of the general formula I below:

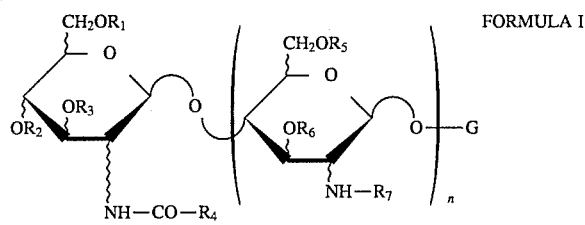

FORMULA I in which:

G is a hexosamine which is variously substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_yCO-$ where x is an integer between 0 and 17, and y is an integer between 1 and 35, or any other acyl group such as for example a carbamyl $R_4$ represents a mono-, di- or triunsaturated aliphatic chain containing at least 12 carbon atoms, and n is an integer between 1 and 4.

According to a preferred embodiment of the present invention, G represents:

in *R. meliloti*, an N-acetyl-D-glucosamine 6-sulfate in R. leguminosarum b.v. viciae, an N-acetyl-D-glucosamine.

According to an advantageous form of this embodiment, the lipo-oligosaccharide conforming to the invention is characterized in that it is of the formula (II) below:

FORMULA II

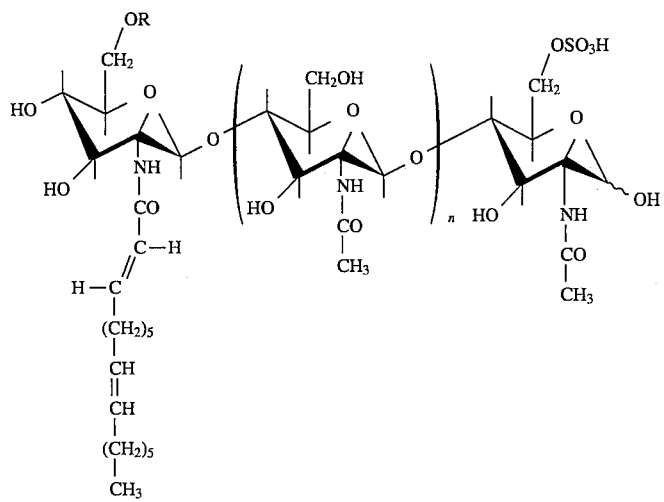

in which R represents H or $CH_3CO-$ and n is equal to 2 or 3.

The *R. meliloti* lipo-oligosaccharides of general formula (II), in which R represents H, are designated below by the general term NodRm; when n=2, the corresponding lipo-oligosaccharide is called NodRm-1; when n=3, the corresponding lipo-oligosaccharide is called NodRm-3.

The lipo-oligosaccharides of general formula (II), in which R represents $CH_3CO-$, are designated below by the general term Ac-NodRm; when n=2, the corresponding lipo-oligosaccharide is called Ac-NodRm-1; when n=3, the corresponding lipo-oligosaccharide is called Ac-NodRm-3.

The aim of the present invention is also to provide processes for producing the essentially pure substances conforming to the present invention, the said processes include purification processes using Rhizobiaceae culture supernatants as starting material, routine processes using sequential or convergent synthesis in oside syntheses and processes for producing said substances by genetic engineering using as starting material the nod genes cloned into microorganisms belonging to the Rhizobiaceae family or otherwise, optionally under the control of an appropriate promoter and/or in the presence of regulatory genes which have been subjected to appropriate mutations.

According to an advantageous embodiment of a process for producing the essentially pure substance conforming to the present invention, during a first stage, a recombinant plasmid is produced which results from the cloning, into a plasmid capable of replicating in a Rhizobiaceae bacterium or any other appropriate bacterium, (1) either of a fragment which contains common and specific nod genes as well as the regulatory genes of a given Rhizobiaceae bacterium, or (2) of the regulatory genes for the express ion of the nod genes. The Rhizobiaceae bacteria or any other appropriate bacteria are then modified by introducing the said recombinant plasmid in order to obtain a mutant strain which highly overproduces Nod factors and the said mutant strain is cultured in an appropriate culture medium; during a second stage, the culture supernatant is recovered and it is purified by extraction with an appropriate lower alcohol, or by solid-liquid extraction followed by a reversed-phase HPLC chromatography of the extraction residue, a gel permeation chromatography, an ion-exchange chromatography and a reversed-phase analytical HPLC chromatography.

According to an advantageous embodiment of this process, the Nod factor-overproducing plasmid is introduced into a non-exopolysaccharide-producing mutant Rhizobiaceae bacterium.

According to another advantageous embodiment of the process for producing the substantially pure substance conforming to the present invention, a wild strain of Rhizobiaceae bacteria, which are highly productive of Nod factors, is used as starting material, the said strain being cultured in an appropriate culture medium, after which the culture supernatant is recovered and treated using the methods indicated above.

The subject of the present invention is also a plant-treatment agent, the or an active constituent of which is an essentially pure substance as defined above, and in particular:

an agent for stimulating the mechanisms for defending the plants against pathogens, an agent for stimulating the symbiotic properties of Leguminoseae, especially with respect to nitrogen fixation.

According to an advantageous embodiment of the plant-treatment agent conforming to the present invention, it is formulated in the form of a composition for coating seeds or an aqueous solution or suspension for spraying, in which the said substance is present alone or combined with other active constituents.

According to another advantageous embodiment of the plant-treatment agent conforming to the present invention, the said substance is present in the coating compositions or the aqueous solutions or suspensions at a concentration of between $10^{-6}M$ and $10^{-14}M$ when the plant-treatment agent is intended to be used as agent for stimulating the defence mechanisms or the symbiotic properties.

Furthermore, the subject of the present invention is a therapeutic agent, the or an active constituent of which is an essentially pure substance as defined above.

According to an advantageous embodiment of this therapeutic agent, the said substance is present in the therapeutic agent at a concentration of between $10^{-5}M$ and $10^{-8}M$.

In addition to the above provisions, the invention also comprises other provisions which will become apparent from the description below.

The invention will be understood more clearly with the aid of the additional description below which refers to the examples below.

EXAMPLES

It should be clearly understood, however, that these examples, as well as the appended drawings, are given solely as illustration of the subject of the invention and do not constitute in any manner a limitation thereof.

EXAMPLES

Example 1 - Preparation of the compounds conforming to the invention by purification using as starting material a *Rhizobium meliloti* culture medium.

A. Production of the compound

The production of extracellular Nod factors by Rhizobium is under the control, on the one hand, of the common genes nodA,B,C (van Brussel et al., J. Bacteriol., 1986, 165, 517–522; Zaat et al., J. Bacteriol., 1987, 169, 3388–3391; Faucher et al., J. Bacteriol., 1988, 170, 5489–5499) and, on the other hand, of the host-specific nod genes, for example *R. meliloti*, the nodH and nodQ genes (Faucher et al., J. Bacteriol., 1988, 170, 5489–5499; Faucher et al., Molec. Plant-Microbe Interact., 1989, 2, 291–300).

Regulation of the transcription of the common genes nodA,B,C is under the control of the regulatory proteins encoded by the nodD1, nodD2, nodD3 and syrM genes (Mulligan et al., PNAS, 1985, 82, 6609–6613; Gyorgypal et al., Mol. Gen. Genet., 1988, 212, 85–92). The protein NodD1 is active only in the presence of certain inductive flavonoids such as luteolin, which are present in the root exudates of Leguminoseae (Mulligan et al., PNAS, 1985, 82, 6609–6613; Peters et al., Science, 1986, 233, 977–980). The presence of the nodD3 and syrM genes in the multicopy plasmid brings about a constitutive activation of the nodA,B,C genes even in the absence of inductive flavonoids (Mulligan et al., Genetics, 1989, 122, 7–18).

To determine the regulation of the other nod genes, the inventors constructed fusions between the genes for host specificity nodE, nodG and nodH and the lacZ gene from E. coli which encodes for β-galactosidase. These fusions made it possible to show that in *R. meliloti*, the nod genes for host specificity are regulated in the same way as the common genes nodA,B,C: (i) their transcription is activated by nodD1, nodD3 and syrM, (ii) luteolin is required for activation by nodD1, (iii) the activation of transcription is much higher when the regulatory genes and the structural genes are in a plasmid of the incompatibility group Inc-P1 (present at 5–10 copies per cell).

This information prompted the inventors to choose a plasmid pRK290, derived from pRK2, in which a 30-kb fragment of the nod region of the *R. meliloti* megaplasmid pSym was cloned. This recombinant plasmid, pGMI149, contains the entire common and specific nod genes as well as the regulatory genes nodD1, nodD3 and syrM (Debellé et al., J. Bacteriol., 1986, 168, 1075–1086; Faucher et al., J. Bacteriol., 1988, 170, 5489–5499). They have shown that *R. meliloti* strains which contain the plasmid pGMI149 overproduce Nod factors: indeed, their production is at least one hundred times greater compared with wild *R. meliloti* strains.

For large scale production of Nod factors, for example for fermenter cultures, the high production of exopolysaccharides can present disadvantages for the filtration of the cultures and for the purification of the signal molecules. The inventors therefore thought it preferable to introduce the overproducing plasmid pGMI149 into the *R. meliloti* mutant EJ355 which does not produce exopolysaccharides. The strain EJ355 (pGMI149) produces Nod factors in abundance but no exopolysaccharides.

By using gene fusions between the nod genes from *R. meliloti* and the lacZ gene from *Escherichia coli* (nod::lac fusions) to measure the level of expression of the nod genes, the inventors developed a culture medium which permits good expression of the nod genes and a high production of Nod factors. A satisfactory medium is an inorganic medium which contains succinate as carbon source and glutamate as nitrogen and carbon source. Indeed, in a rich medium, containing protein lysates and yeast extracts, the activation of the transcription of the nod genes is lower; furthermore, the purification of Nod factors is easier using culture supernatants prepared from simple media. The composition of this medium is for example as follows:

inorganic salts: 14.7 mM $KH_2PO_4$; 11.5 mM $K_2HPO_4$; 1 mM $MgSO_4$; 0.46 mM $CaCl_2$; 37 μM $FeCl_3$, organic compounds: 5.3 mM sodium L-glutamate; 7.4 mM sodium succinate; 2 μM biotin; 10 μM luteolin.

B.1. Purification of the compound

B.1.1. The compound is extracted from the *Rhizobium meliloti* culture medium (15 l) using butanol (2 extractions with 3 liters of BuOH). The butanolic phase is washed with water (1 liter) and then concentrated under vacuum. The residue obtained is dissolved in water (500 ml) and extracted 2 times with ethyl acetate (2 times 300 ml). The aqueous phase is finally concentrated and then freeze-dried.

B.1.2. Reversed-phase HPLC chromatography

The residue obtained by butanolic extraction is chromatographed by reversed-phase HPLC on a 10 μm μ-Bondapak $C_{18}$ column—Water Associates—7.5×250 mm, with a flow rate of 2 ml/min and using a linear gradient from an 80-20 water-ethanol mixture A to pure ethanol B (FIG. 1.1); the detection is carried out at 220 nm. The area presenting biological activity is collected for further purifications.

B.1.3. Gel permeation chromatography

The fraction is purified by gel permeation on a Sephadex LH20 column (1×20 cm column; LH20 phase, Pharmacia) in a solvent such as ethanol, at a flow rate of 4 ml/hour. The detection is carried out at 220 nm. The column was calibrated beforehand with respect to polyethylene glycol (PEG) standards (cf. FIG. 1.2). The active shaded fraction is collected.

B.1.4. Ion-exchange chromatography

The active compound (shaded area) is eluted on an ion-exchange column (1×2 cm DEAE-Trisacryl column; IBF) with a linear NaCl gradient between 0 and 0.1N in a $5 \times 10^{-3}$N Tris-HCl buffer, pH=8.2 (FIG. 1.3).

B.1.5. Reversed-phase analytical HPLC chromatography

The final purification step is a reversed-phase HPLC chromatography on an analytical column (4.5×250 mm; 5 μm Spherisorb/$C_{18}$ phase) with an 80-20 water-acetonitrile mixture as solvent at a flow rate of 1 ml/min; 300 μg are injected (FIG. 1.4a). Two peaks absorbing at 220 nm are thus detected and exhibit biological activity. Structural study will show that it is in fact the same compound appearing in two forms in equilibrium (free α and β anomeric forms).

B.2. Analysis of the constituents

B.2.1. Analysis of the monosaccharides

After complete hydrolysis of the compound (3N HCl; 3 h; 100° C.) and then derivatization to peracetylated methyl glycoside, a single monosaccharide, identified as being 2-deoxy-2-acetamidoglucose or acetyl glucosamine (NAc Glc), is observed by vapor-phase chromatography. This sugar was shown to be of the D series after preparation of the glucoside peracetate with a chiral alcohol and comparison, using VPC, with (−)-2-butanol-N-acetylglucosamine standards of the D and L series derived in a similar manner.

Reduction of the compound with sodium borodeuteride (1N $NaBD_4/H_2O$; 18 h; 20° C.) is followed by controlled methanolysis (1N MeOH/HCl; 80° C.; 1 h) and then by a water-dichloromethane partition. The aqueous phase contains 1-0-Me-NacGln and 2-deoxy-2-acetamidoglucitol which are identified by VPC (FIG. 2.1); identification by VPC is carried out on a 0.32 mm×30 m OV1 column using helium and an FID detector. The organic phase contains the methyl glycoside of the glucosamine which is N-acylated by a $C_{16:2}$ fatty acid and which is identified by its electron impact mass spectrum on the pertrimethylsilylated derivative using data from the literature (Demary, M. et al., Nouv. J. Chimie, 1977, 2, 373–378); the electron impact mass spectrum (EI-MS) of the 1-OMe glucosamine, which is amidated on the nitrogen atom by a fatty acid and pertrimethylsilylated, is represented in FIG. 2.3. After catalytic hydrogenation of the side chain, methanolysis (MeOH, 3N HCl; 2 h; 100° C.) and then acetylation, VPC analysis—carried out on a 0.32 mm×30 m OV1 column using helium and an FID detector—of the peracetylated derivatives makes it possible to confirm the structure of this N-acyl-sugar by visualizing 1-OMe-GlcNAc and methyl palmitate (accompanied by methyl stearate in a smaller quantity) (FIG. 2.2).

Figure 3:
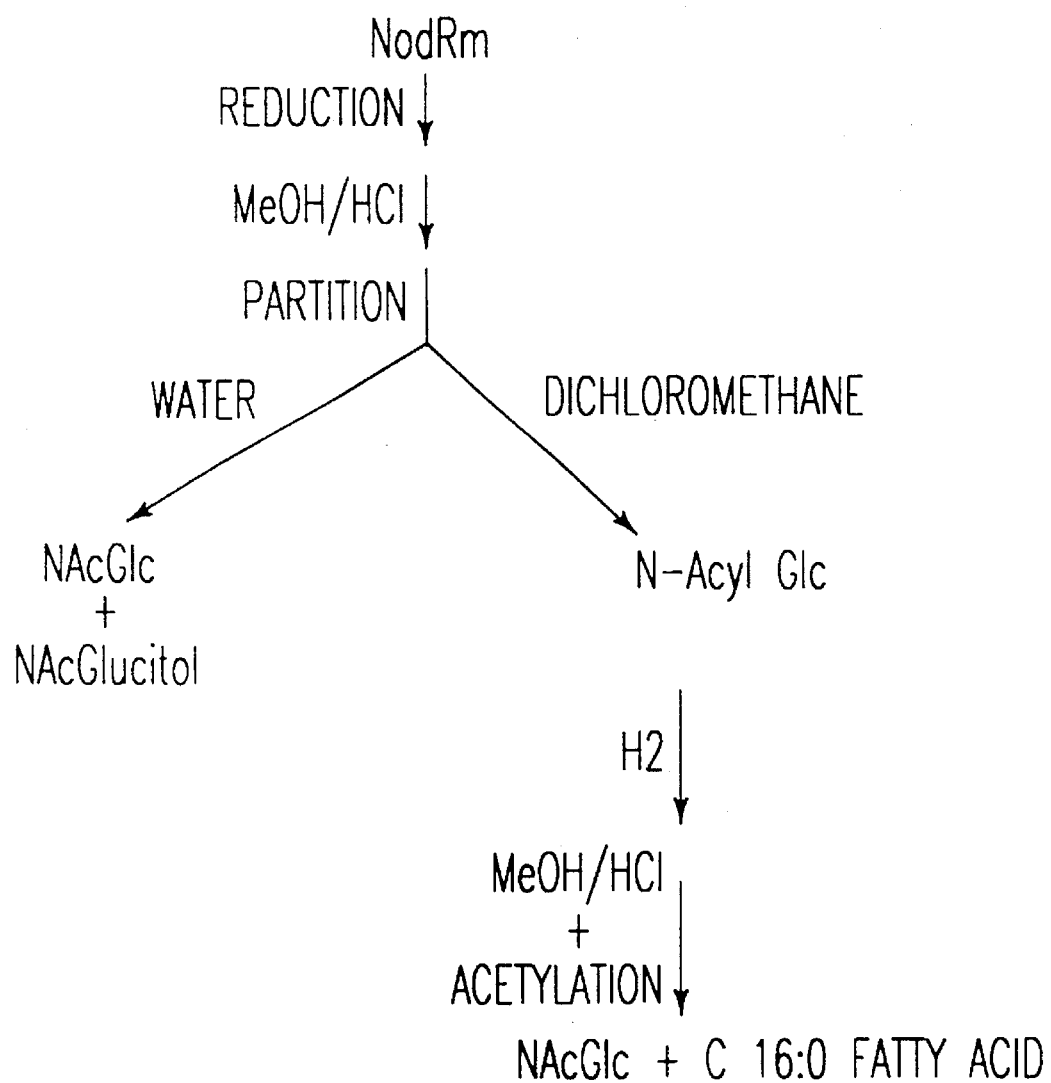
FIG. 3 is a flow chart depicting the three types of glucosamine present in the compound of Example B.2.1.

This analysis makes it possible to establish the presence of three types of glucosamine: NAcGlc, reducing NacGlc and N-acyl Glc, using an analytical procedure summarized in FIG. 3 which is appended.

B.2.2. Fatty acid composition

It was possible for the fatty acids present in the compound to be isolated after saponification (5% KOH; 18 h; 80° C.) and then analyzed by VPC—on a 0.32 mm×30 m OV1 column using helium and an FID detector—in the form of methyl esters (FIG. 2.4). This study made it possible to identify, in addition to a predominant $C_{16:2}$ fatty acid, other minor entities: $C_{16:0}$, $C_{16:1}$, $C_{18:0}$ and $C_{18:1}$. It was possible for the position of the two double bonds of the $C_{16:2}$ fatty acid to be specified from the MS—MS mass spectrum of the carboxylate formed from its perfluorobenzyl ester (J. C. Promé et al., Rapid Comm. Mass Spectrom., 1987, 1, 80–82) and localized in 2 and 9 of the chain.

B.2.3. Detection of a sulfate functional group

After culturing the bacteria in the presence of $^{35}S$-labeled sodium sulfate and then purification of the compound, the observed correlation between the UV-absorption profile and $^{35}S$-incorporation makes it possible to establish the presence of a sulfate functional group in this compound. FIG. 1.4b represents the said correlation which is obtained by incorporation of $^{35}S$, after culturing on $(^{35}S)$-$Na_2SO_4$ and then fractionating on the basis of the profile represented in FIG. 1.4a and counting the radioactivity by liquid scintillation.

B.2.4. Determination of the mode of interglycoside bonding

The mode of bonding between the various glucosamines was established after permethylation of the $NaBD_4$-reduced compound, hydrolysis and preparation of the alditol acetates according to previously-described methods (K. Stellner et al., Arch. Blochem. Biophys., 1973, 155, 464–472), followed by a VPC-MS analysis; the electron impact mass spectrum of the alditol acetates obtained from permethylation of the reduced compound is represented in FIG. 2.5. This study made it possible to identify alditol acetates which are tetramethylated in positions 1, 2, 3 and 5 (spectrum a) and 2, 3, 4 and 6 (spectrum b) and tri-O-methylated in positions 2, 3 and 6 (spectrum c), derived respectively from a reducing glucosamine which is substituted in positions 4 and 6, a terminal glucosamine and a glucosamine which is bonded in positions 1 and 4.

B.3. Mass spectrometry

B.3.1. Positive mode FAB mass spectrometry

Figure 4A:
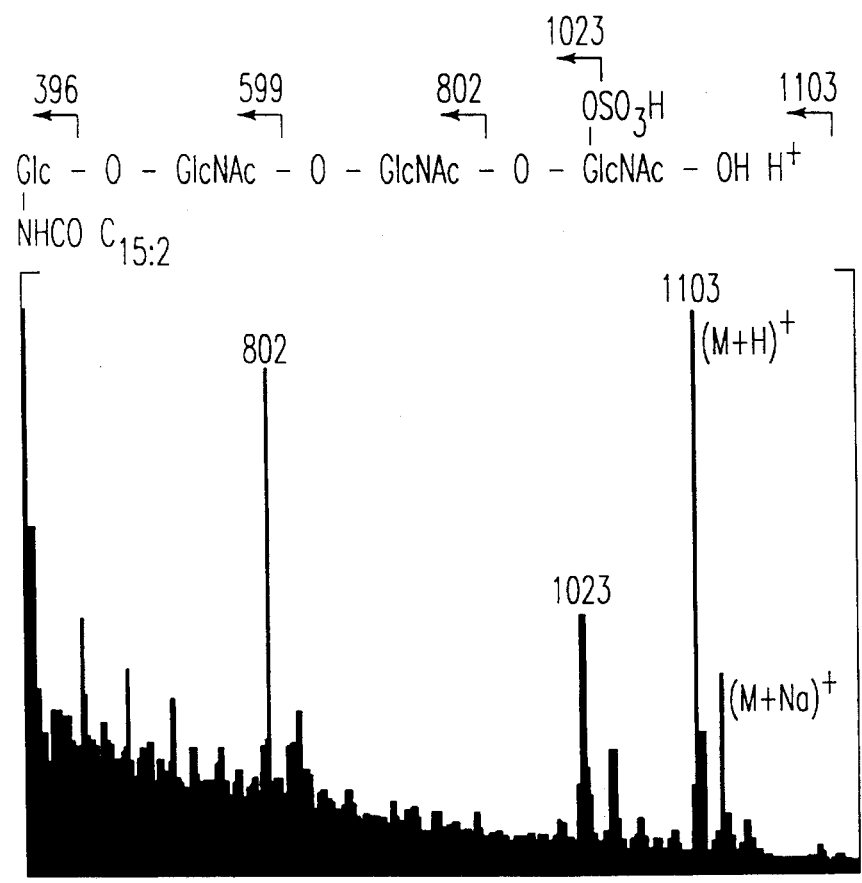
FIGS. 4A–C are spectra of the compound described in Example B.3; 4A is a FAB mass spectrum; 4B is a MS—MS spectrum.
Figure 4B:
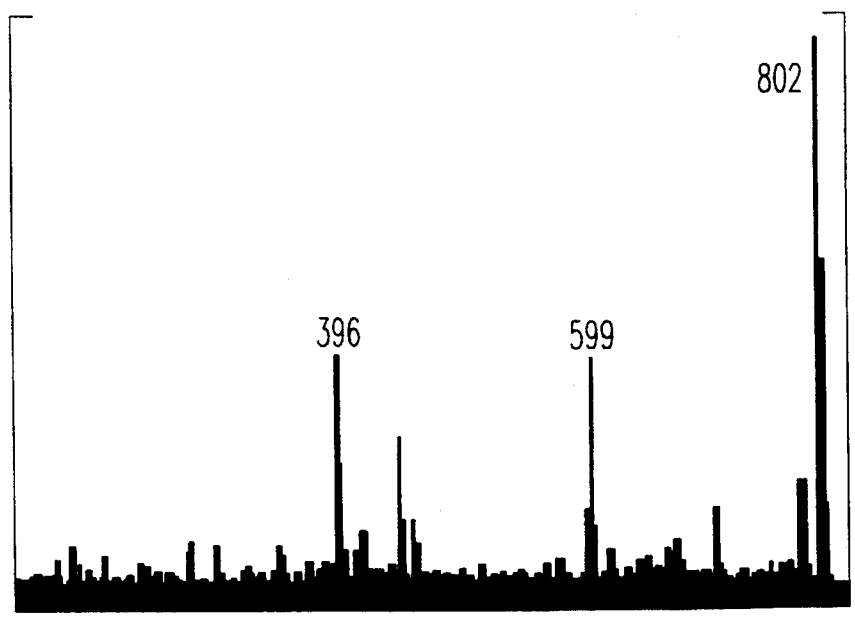
Figure 4C:
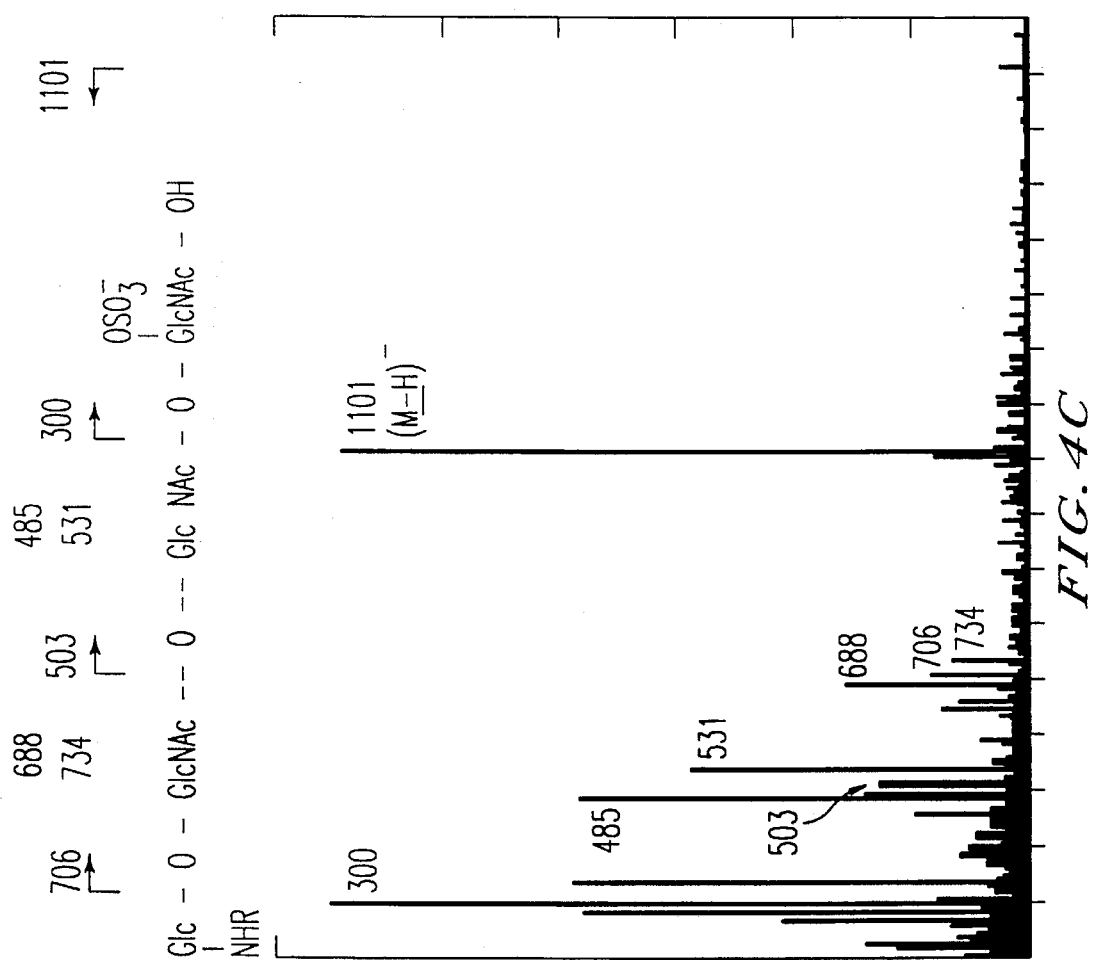
Figure 5A:
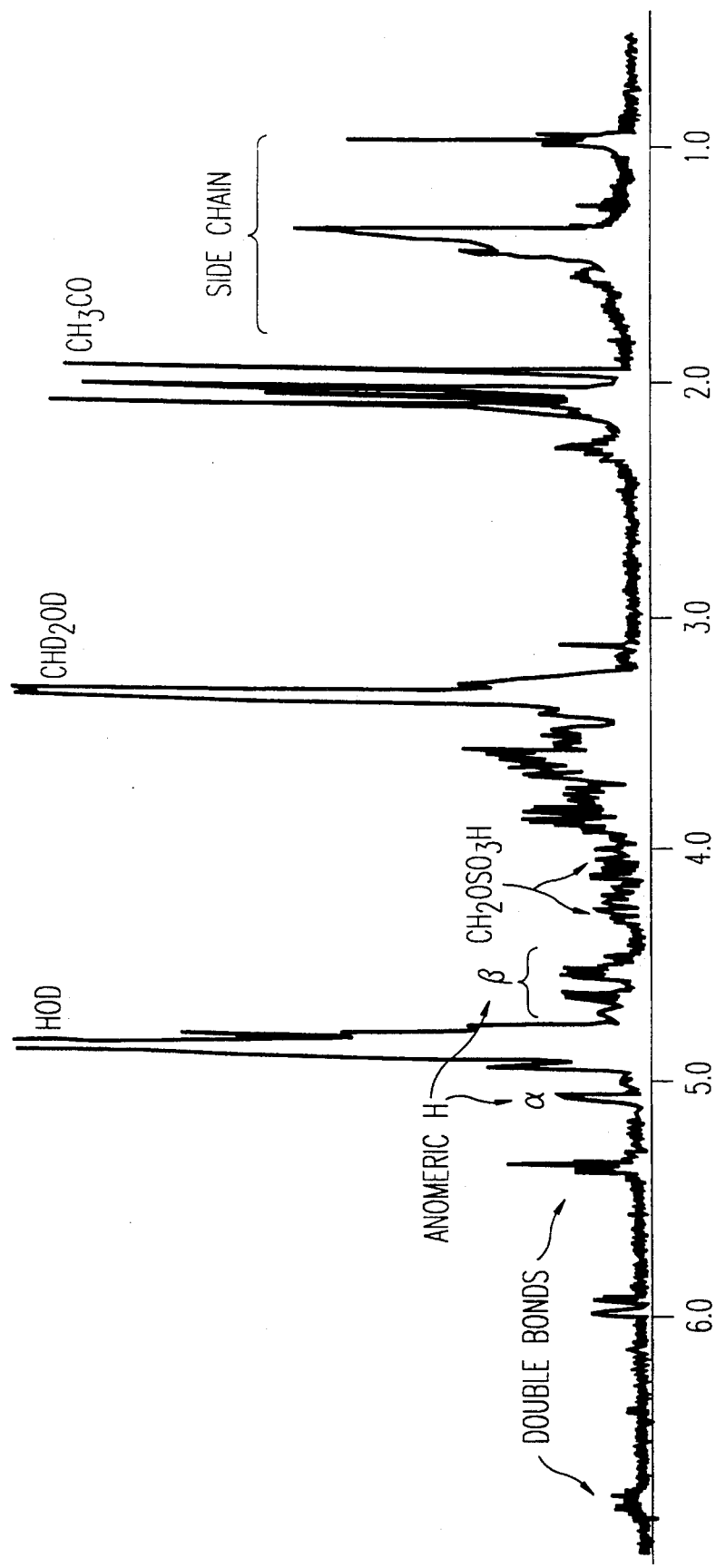
FIGS. 5A–5F are NMR spectra of the compound described in Example B.4. 5A is a $^1$H NMR spectrum; 5B and 5C are a COSY $^1$H homonuclear 2D-NMR spectra; and 5D–5F are $^{13}$C NMR spectra.
Figures 5B, 5C:
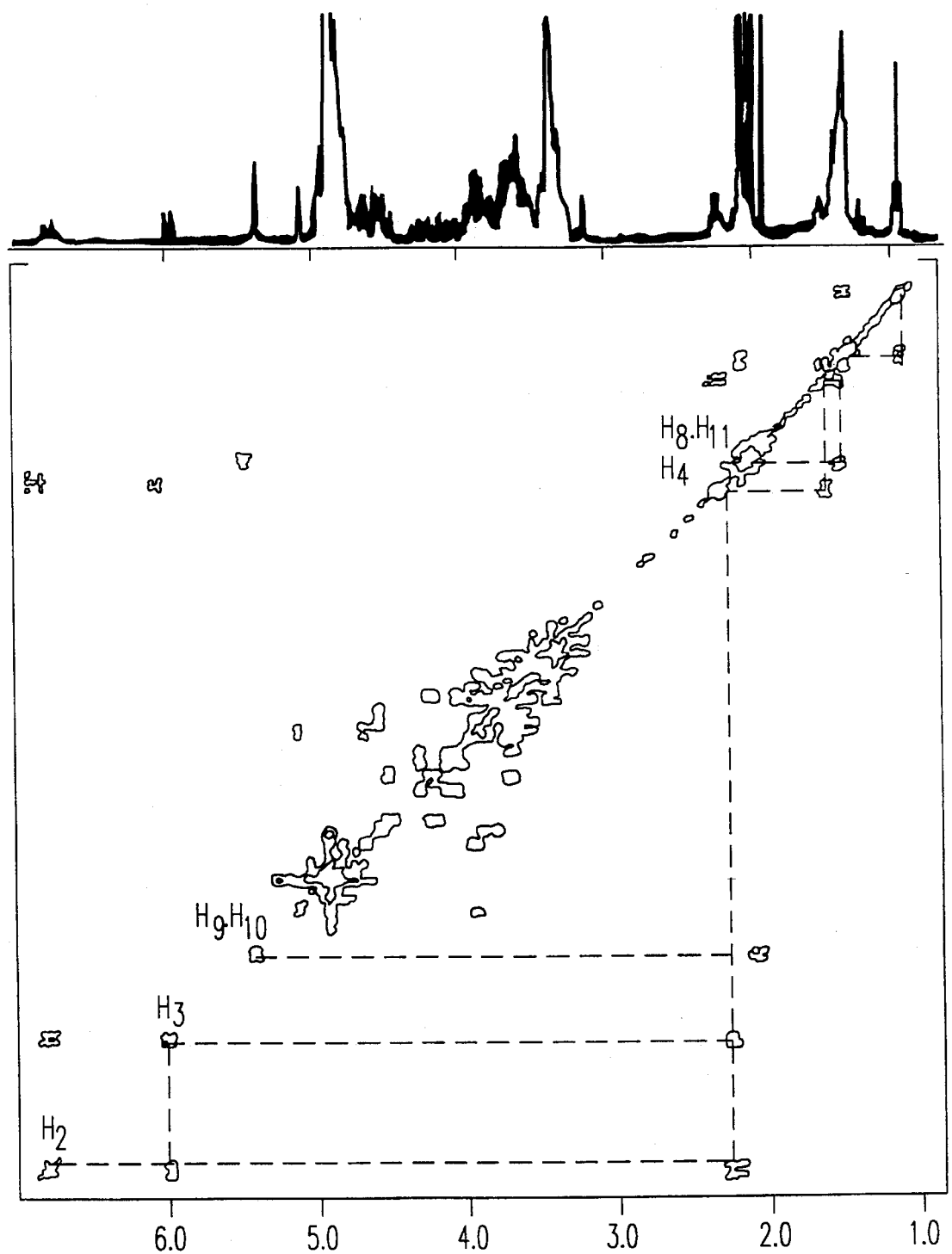
Figure 5D:
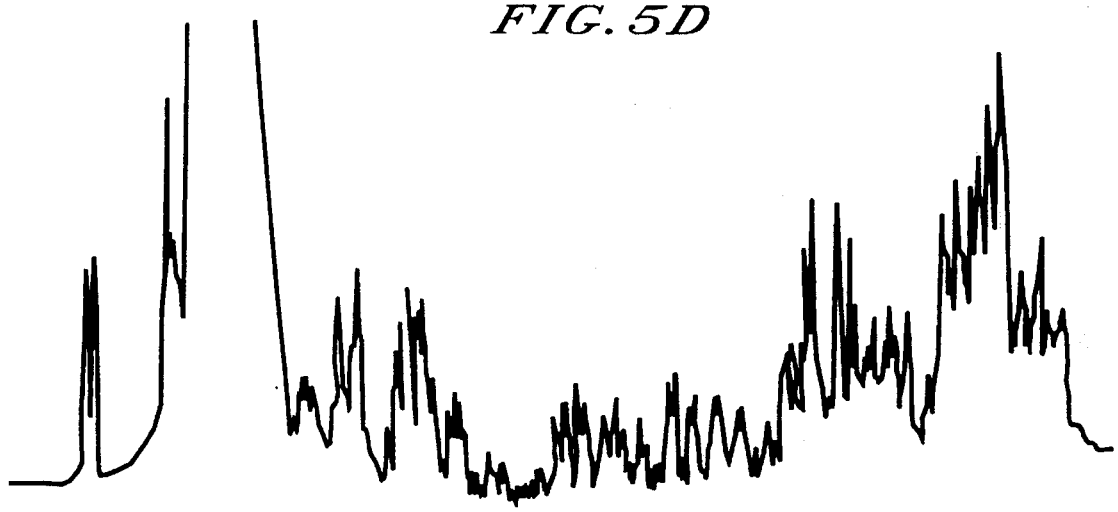
Figure 5E:
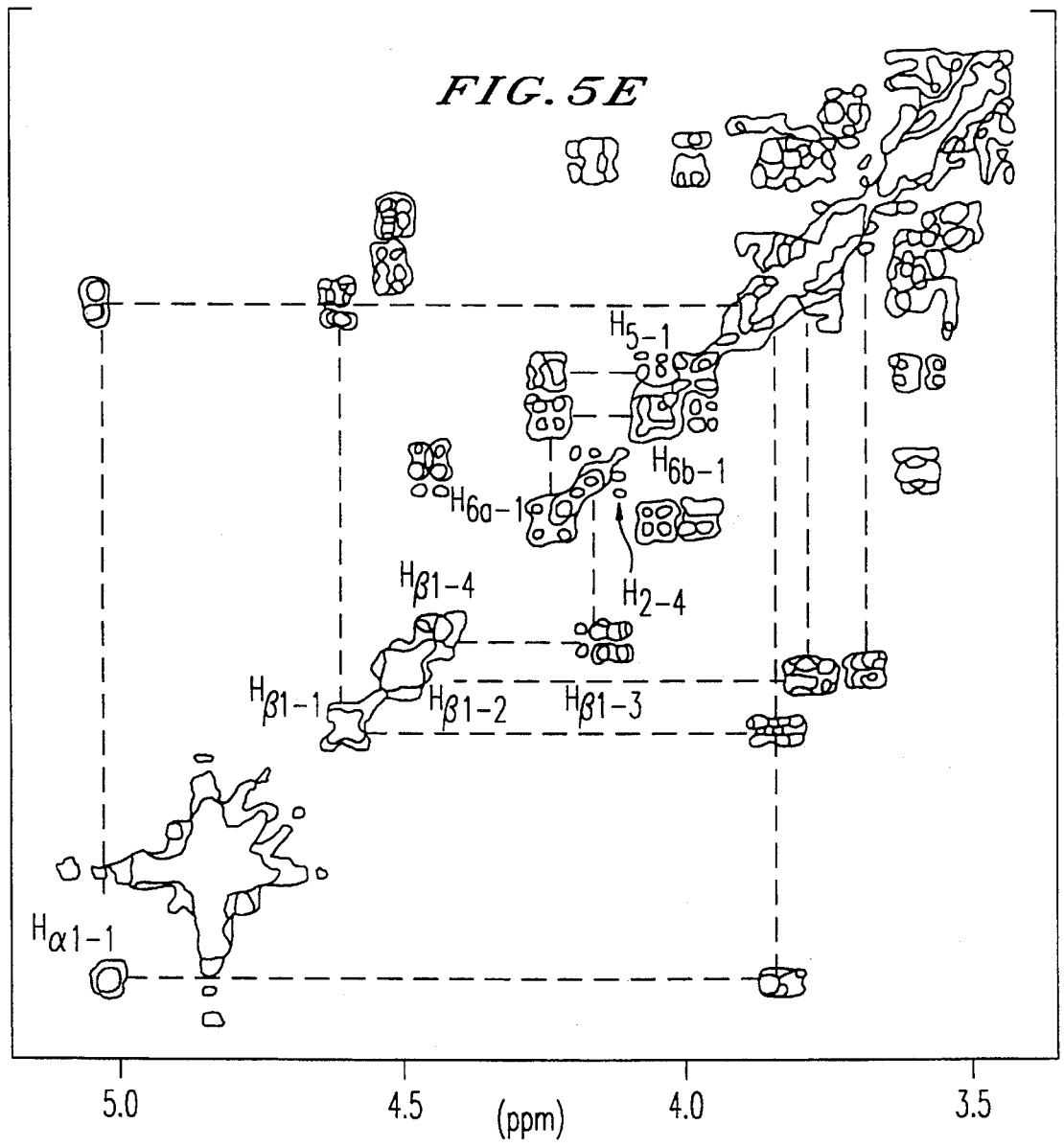
Figure 5F:
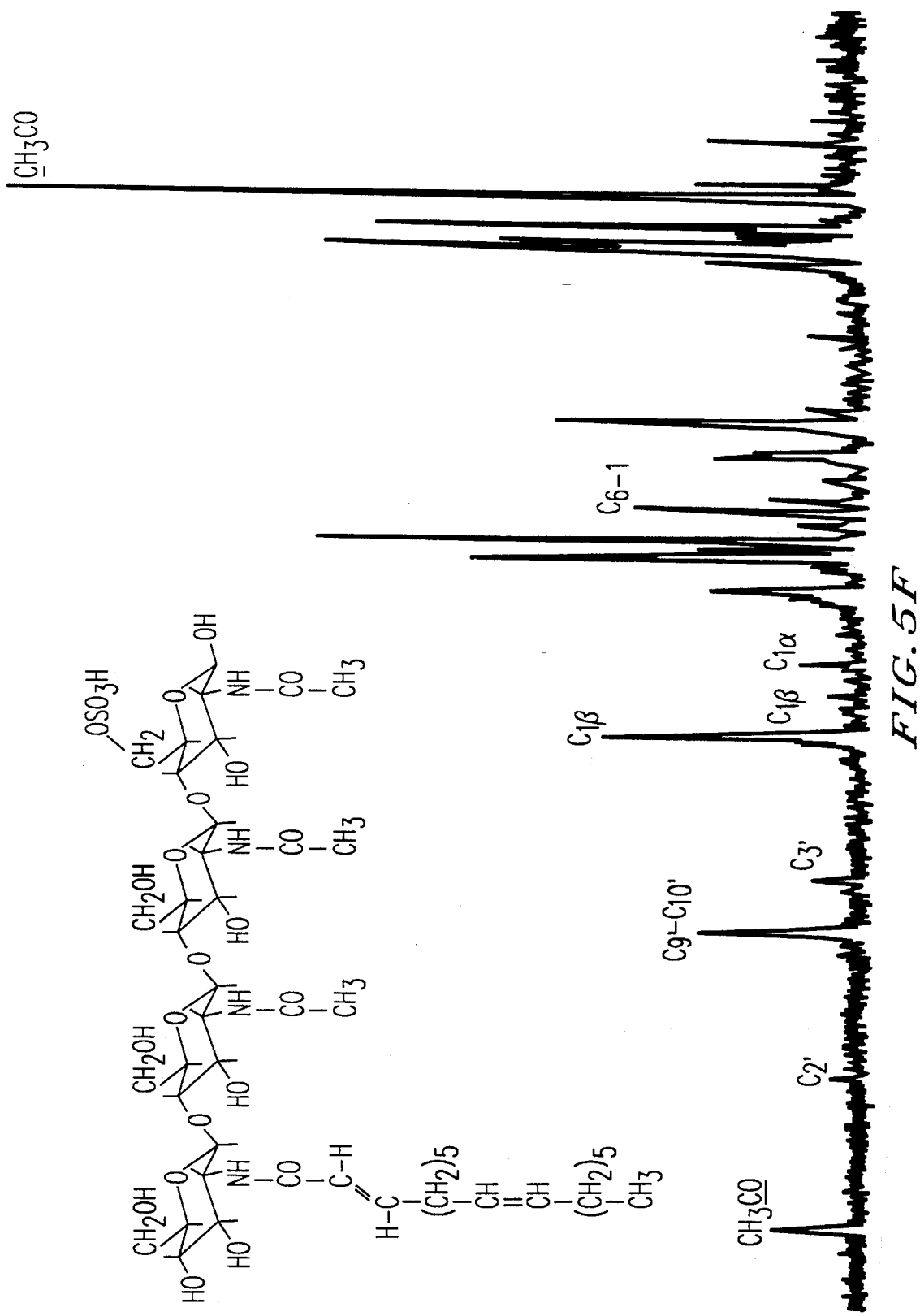

The positive mode FAB mass spectrum of the compound (FIG. 4.1, scanning from m/z 4,000 to m/z 100 (nominal mass)) shows a pseudomolecular ion $(M+H)^+$, m/z=1103, accompanied by a sodium-containing ion corresponding to m/z=1125. Fragment ions are also observed at m/z=1023 and 802, which are attributed to sulfate and NAcGlucosamine sulfate losses respectively. Decomposition of the m/z=802 ion is observed by MS—MS spectrometry (FIG. 4.2; B/E scan) and leads to two glycosilyl fragments at m/z=599 and 396 following the breaks between the various monosaccharides. These two spectra make it possible to establish a linear tetrasaccharide structure whose reducing sugar is substituted by a sulfate functional group, and the terminal sugar by a $C_{16:2}$ fatty acid.

B.3.2. Negative mode FAB mass spectrometry

Apart from the pseudomolecular ion $(M-H)^-$ at m/z=1101, the negative mode FAB spectrum exhibits fragments which are attributable to the glycoside cavities. Analysis of these ions leads to structural conclusions similar to those described above: cf. FIG. 4.3 which shows the negative FAB ionisation mass spectrum, using thioglycerol as matrix.

B.4. NMR

B.4.1. $^1H$ NMR and proton homonuclear 2D-NMR (COSY)

The data relating to the $^1H$ NMR and COSY-NMR spectra make it possible to establish the following structural elements:

a) The side chain exhibits in $^1H$ NMR two types of vinyl protons corresponding to the two double bonds. Two low-field signals ($\delta$=5.95 ppm; 1 H and $\delta$=6.80 ppm; 1 H) are attributed to a double bond conjugated to the carbonyl functional group and they possess a large coupling constant (J=15 Hz) characteristic of an E configuration; FIG. 5.1 represents the abovementioned $^1H$ NMR spectrum; $CD_3OD$ is used as solvent and a frequency of 300 MHz is used ("Bruker" apparatus). The two magnetically equivalent protons of the double bond inside the chain appear as a single signal ($\delta$=5.35 ppm). The protons of these two double bonds exhibit, in 2D-COSY, a series of correlations with the other aliphatic protons which is characteristic of a linear chain; FIG. 5.2 represents the COSY $^1H$ homonuclear 2D-NMR spectrum obtained using $CD_3OD$ as solvent and a frequency of 300 MHz ("Bruker" apparatus).

b) Anomeric protons: the COSY $^1H$ homonuclear 2D-NMR spectrum of the saccharide region is represented in FIG. 5.3; this spectrum, which was obtained using $CD_3OD$ as solvent and a frequency of 300 MHz ("Bruker" apparatus), shows, in the 3.4 to 5.2 ppm saccharide proton region, 5 signals having only one correlation, which are attributed to the anomeric protons. Furthermore, no signal is masked by the unresolved complex for water, as indicated by the lack of correlation in this region of the spectrum. These anomeric signals correspond to three doublets of the $\beta$ bonds ($\delta$=4.40 to 4.55 ppm; 3 H; J=8.5 Hz) and two doublets attributed to the anomeric protons of the $\alpha$ and $\beta$ forms ($\delta(\alpha)$=5.05 ppm; J=3.4 Hz and $\delta(\beta)$=4.60 ppm; J=8.5 Hz).

c) Protons of the rings: the saccharide rings are characterized by the methyl signals of the acetamide groups, which are split by the coexistence of the free $\alpha$ and $\beta$ forms of the oligosaccharide ($\delta$=2.0 to 2.15 ppm; 6s; 9H). The other protons of the ring resonate between 3.2 and 3.9 ppm. Only three signals, which are more unmasked, are attributed to the hydrogens situated near the sulfate group. The correlation mode observed by 2D-COSY (FIG. 5.3) between these three signals is characteristic of protons 5 and 6 (H5/H6b, H5/H6a and H6a/H6b correlation). This result makes it possible to place the sulfate functional group in position 6.

B.4.2. $^{13}C$ NMR

Attribution of the various signals of the proton-decoupled $^{13}C$ NMR spectrum (FIG. 5.4) made it possible to confirm the presence of a di-unsaturated fatty acid chain, the $\beta1\rightarrow4$ mode of bonding between the glucosamines as well as the position of the sulphate in 6 from the following elements: FIG. 5.4 represents the $^{13}C$ NMR spectrum obtained at 50.4 MHz ("bruker" apparatus) using $D_2O$ as solvent:

a) Fatty acid chain: the chemical shifts of the carbons of the side chain ($C_{2'}$ to $C_{16'}$) are characteristic of a fatty acid possessing a conjugated double bond ($C_{2'}$ and $C_{3'}$; $\delta=125$ and 155 ppm) and an inner double bond ($C_{9'}$ and $C_{10'}$; $\delta=133$ ppm).

b) Anomeric carbons: a preponderant signal ($\delta=103.7$ ppm) which is attributed to the anomeric carbons of the nonreducing monosaccharides exhibits a chemical shift which is similar to the $C_1$ of the methyl glucopyranoside of NAcGlc. Two signals, of lower intensities, are attributed to the $C_1$ of the reducing glucosamine appearing in these two free anomeric forms ($\delta C_1\alpha=93.1$ ppm and $\delta C_1\beta=97.8$ ppm).

c) Ring: from the literature data, attribution of the various signals leads to confirmation of the $\beta 1\rightarrow 4$ linkage in the tetrasaccharide. This attribution is complicated by the separation, into two groups of signals, of the carbons of the reducing glucosamine. The presence of the sulfate functional group in position 6 is supported by the observed unmasking of carbon 6 which carries this functional group ($\delta C_{6-1}=68.7$ ppm).

Example 2 - Detection of the biological activity of the NodRm-1 factor

The biological activities detected (i) by the specific activity test of deformation of the root hairs (Had) on vetch, described by Zaat et al., (J. Bacteriol., 1987, 169, 3388–3391), (ii) and by the tests of deformation and ramification of lucerne root hairs, described by Faucher et al. (J. Bacteriol, 1988, 170, 5489–5499; Molec. Plant-Microbe Interact., 1989, 2, 291–300), proved that the substance conforming to the invention is a plant-specific symbiotic signal whose production is under the control of the nod genes.

Indeed:

1) after three types of purifications based on various physicochemical properties, ion-exchange, gel filtration and reversed-phase chromatography, an absolute correlation is observed, in all cases, between the presence of this molecule—characterized by its HPLC profile, by mass spectrometry and by $^1$H NMR spectrometry—and its specific Had activity on lucerne;

2) an increase in the activity of the nod genes, either by induction of transcription or by increasing the number of copies of these genes, is correlated with an increase in the production of the molecule, whereas a mutation due to the Tn5 transposen in the nodA or nodC genes has the effect of suppressing its production;

3) the biological activity of the compound NodRm-1, as detected by the root hair ramification bioassays, is very high and specific.

A NodRm-1 solution, at a concentration of the order of $10^{-8}-10^{-10}$M, causes Had reactions in lucerne, a homologous host, but not in vetch which is a heterologous host. The NodRm-1 compound (see formula II) remains active towards lucerne at a concentration of $10^{-11}$M.

The $^1$H NMR spectrum indicates, for the NodRm-1 compound, a purity of not less than 95% (cf. FIG. 5.1).

Molecules containing an aromatic nucleus, which is characteristic of plant hormones such as auxin and cytokinin, were not detected in the active fraction. Consequently, the possible hormonal contaminants should be present at concentrations of less than $10^{-12}$M, that is to say at concentrations about 1,000,000 times lower than the threshold ($10^{-7}$M) at which these phytohormones act. when they are added by an exogenous route, thus indicating that the observed effects cannot be attributed to such contaminants.

The study of the R. meliloti mutants affected in the host-specific genes reveals an absolute correlation between the specificity of the symbiotic behavior of the living Rhizobium cells and the specificity of the Had bioassay of their sterile supernatants, thus indicating that the Nod signals are involved in inducing the specific infection and the nodulation.

The NodRm-1 compound has both a very high biological activity and a very high specificity. In fact, it causes reactions which can be detected in the host plant at very low concentrations of the order of $10^{-12}$M, whereas known plant hormones such as auxins and cytokinins act at substantially higher concentrations ($10^{-7}-10^{-8}$M). On the other hand, the "elicitor" type oligosaccharides which have been described in the prior art and which act at low concentrations ($10^{-9}$M) are not specific, whereas the signal molecule NodRm-1 conforming to the invention has a high specificity of action: while it acts on lucerne, a homologous plant, at a concentration of $10^{-12}$M, it remains inactive on a non-host plant such as vetch at a concentration of $10^{-8}$M. This molecule therefore exhibits new and important properties with respect to its activity on plants.

In the absence of bacteria and at low concentrations ($10^{-7}$M–$10^{-9}$M), the signal molecule NodRm-1 causes the induction of numerous mitotic divisions in the root cortex of lucerne: NodRm-1 therefore exhibits a high mitogenic effect.

In the absence of bacteria and at low concentrations ($10^{-7}$M–$10^{-9}$M), the signal molecule NodRm-1 causes the induction of nodosity formation in the lucerne roots, which nodosities exhibit ontological, morphological and anatomical characteristics of the lucerne nodosities induced by symbiotic bacteria. NodRm-1 therefore has an organogenetic effect on the lucerne roots.

In the absence of bacteria and at very low concentrations ($10^{-9}$M–$10^{-12}$M), the compound NodRm-1 causes deformations of the root hairs in lucerne and an induction of the transcription of the symbiotic genes of Leguminoseae. At these same doses, in the presence of R. meliloti, the addition of the NodRm-1 compound causes an acceleration of the infection and of the formation of root nodosities. Its addition to Leguminoseae, for example by coating the seeds at the time of sowing, is capable of accelerating the formation of nodosities and the establishment of nitrogen fixation.

It is important to underline that it is the first time that oligomers of sulfated hexosamines are isolated from a bacterium. In fact, sulfated sugars have been isolated from animals but were neither detected nor a fortiori isolated up until now either from plants or from bacteria.

Furthermore, the sulfated and acylated hexosamine oligomers conforming to the present invention exhibit a remarkable biological activity in that they possess an activity at infinitesimal doses; indeed, they are at least 100,000 times more active than plant hormones. The use of natural substances having such an activity at such low doses has never been proposed up until now in the plant sector. This remarkable activity suggests that the substances conforming to the invention have a high affinity for certain receptors—an affinity which is substantially higher than that of the products described up until now, including plant hormones. Receptors which have an affinity for sugars generally possess the structure of glycoproteins and in particular lectins; yet such receptors also exist in the animal kingdom; the substances conforming to the invention must therefore be considered as capable of being endowed with an important therapeutic activity. In particular, the therapeutic agent conforming to the invention is suitable, inter alia, for stimulating the defence mechanisms against pathogens in man and in animals.

Example 3 - Preparation of the substances Ac-NodRm-1 and Ac-NodRM-3 by purification from a *Rhizobium meliloti* culture medium A. Production of the compounds If instead of introducing the "overproducing" plasmid pGMI149 into the *R. meliloti* strain 2011, the plasmid pMH682, which contains only the pair of regulatory genes syrM/NodD3, is introduced, a high increase in the transcription of the common and specific nod genes and an increase in the production of Nod factors are also produced. The butanolic extracts of the supernatant of such a strain exhibit, when they are fractionated by HPLC chromatography, a profile different from that of extracts of the *R. meliloti* strain 2011 (pGMI149), thus implying the production of new compounds.

B. Determination of the structure of the compounds

1. Purification

The compounds are purified according to the procedure described in Example 1. The final reversed-phase analytical HPLC chromatography step makes it possible to separate the Ac-NodRMm-1 compound from the Ac-NodRm-3 compound.

2. Structural studies 2.1. Structure of the AC-NodRm-1 compound 2.1.1. Treatment with sodium methanolate By treating with sodium methanolate, the compound Ac-NodRm-1 is converted to NodRm-1 whose structure is determined as in Example 1.

2.1.2. Mass spectrometry

Figure 6A:
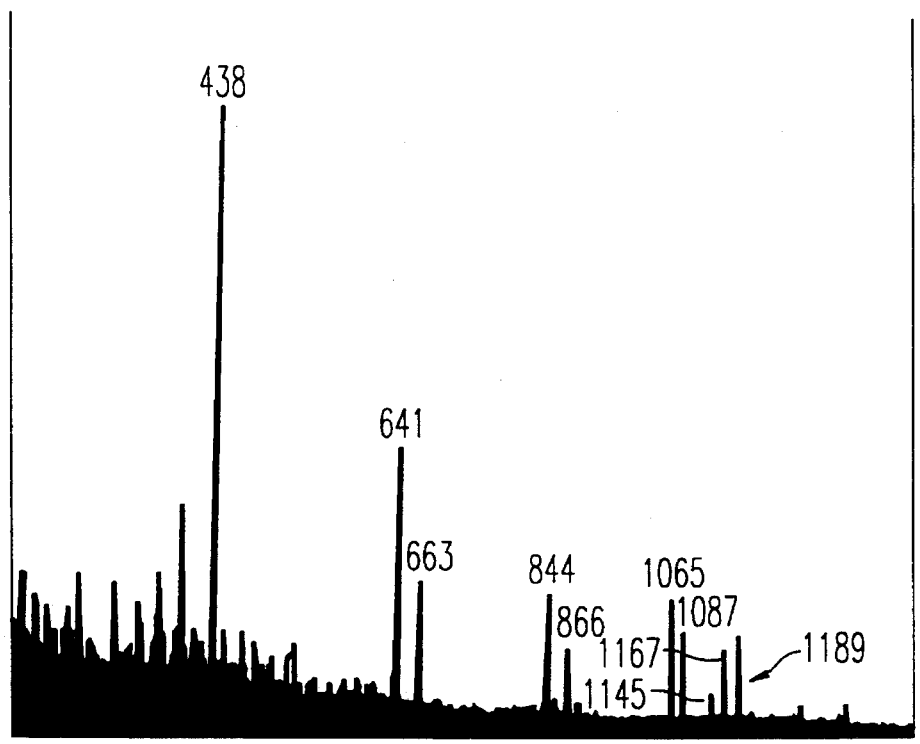
FIGS. 6A and 6B are mass spectra as described in Example 2.1.2. 6A is a positive mode FAB mass spectrum and 6B is MS/MS spectrum.
Figure 6B:
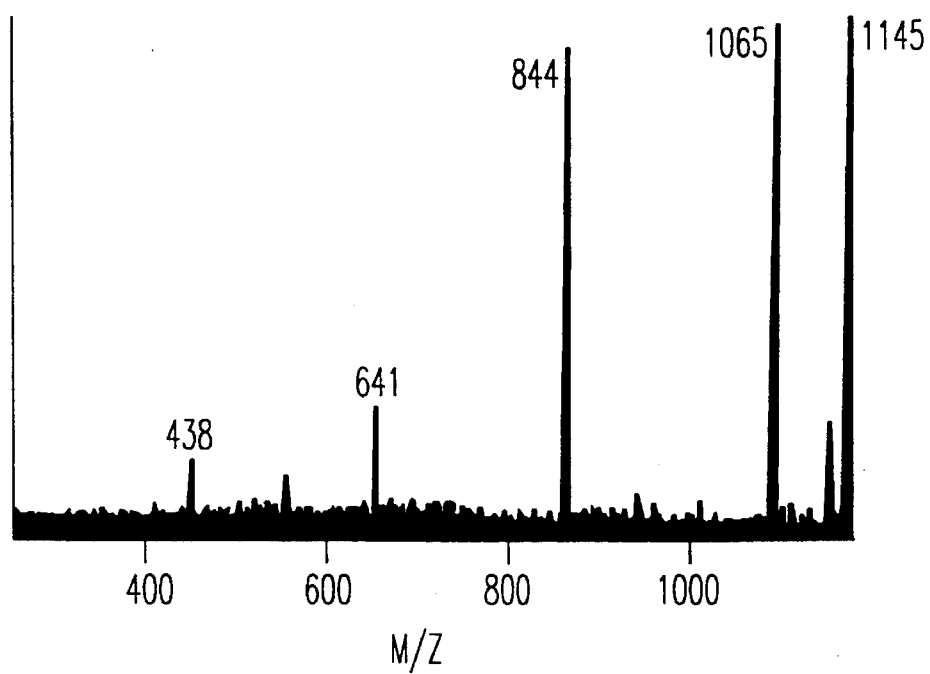

The positive mode FAB mass spectrum of the compound Ac-NodRm-1 (FIG. 6A) shows a protonated molecular ion at m/z 1145, as well as the ions $(M+Na)^+$ at m/z 1167 and $(M+2Na-H)^+$ at m/z=1189. Decomposition of the protonated molecular ion by MS/MS spectrometry (FIG. 6B: B/E scan) leads to fragment ions at m/z 1065, m/z 844, m/z 641 and m/z 438. The fragment ions at m/z 1065 and m/z 884 are attributed to the loss of $SO_s$ and N-acetyl-D-glucosamine sulfate respectively. The fragments at m/z 641 and m/z 438 correspond to the glycosylium ions obtained by breaking the interglycoside bonds. These two spectra show that the compound Ac-NodRm-1 differs from the compound NodRm-1 only by the presence of an acetate group on the nonreducing terminal glucosamine.

2.1.3. $^1$H NMR

The $^1$H NMR spectrum of the compound Ac-NodRm-1 makes it possible to establish the structural elements described in Example 1 (paragraph B.4.1.) for the compound NodRm-1.

(i) two double bonds including one which is conjugated, of E configuration;
(ii) anomeric signals characteristic of β bonding
(iii) signals characteristic of a sulfate group in position 6.

Furthermore, two signals at δ=4.16 ppm and δ=4.46 ppm, which are absent from the spectrum of the compound NodRm-1 and disappearing after O-deacetylation, make it possible to localize the acetate group in position 6 of the nonreducing terminal sugar.

2.2. Structure of the compound Ac-NodRm-3

Figure 7:
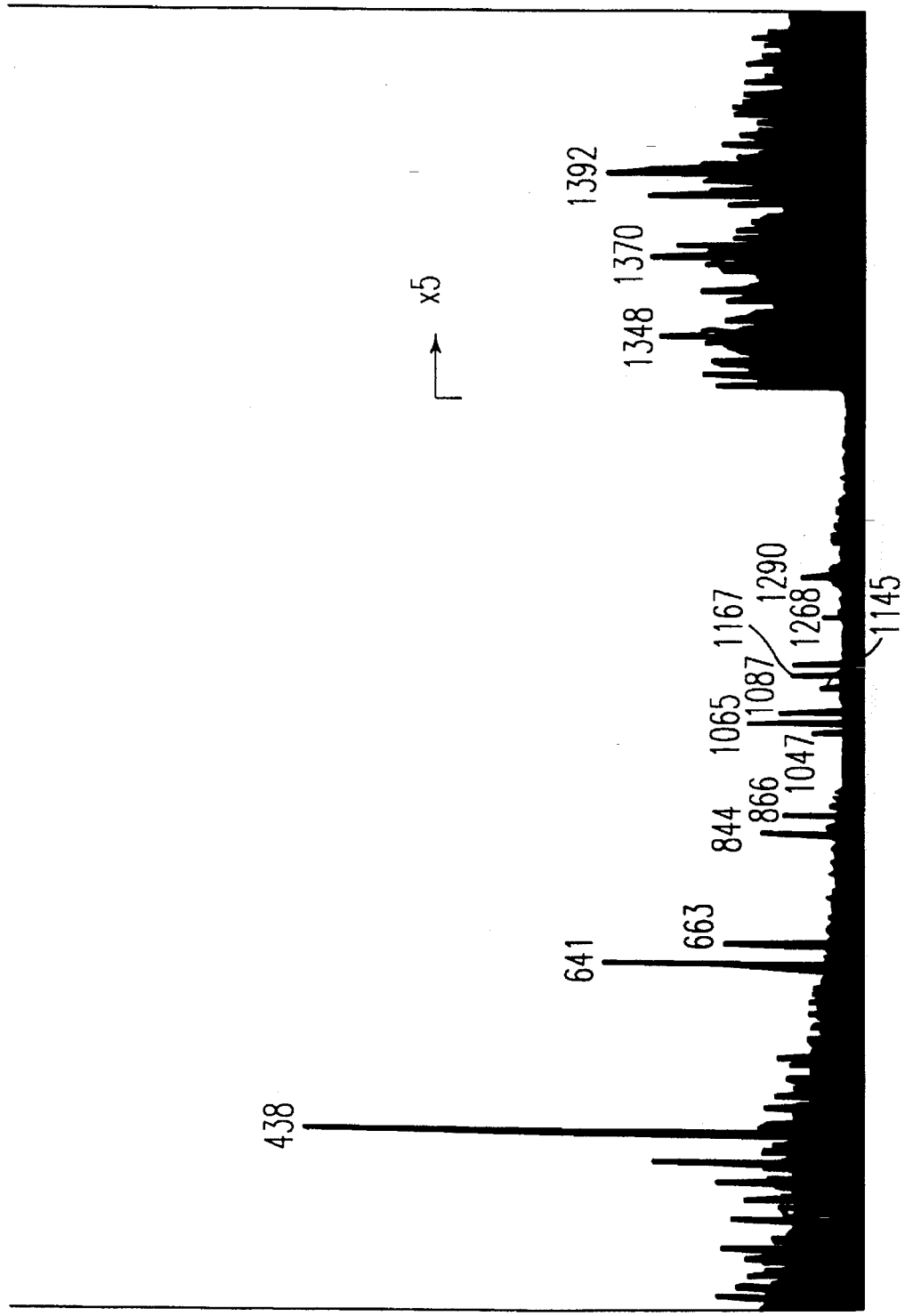
FIG. 7 is positive mode FAB mass spectrum as described in Example 2.2.

The structure of the compound Ac-NodRm-3 was established by positive mode FAB mass spectrometry (FIG. 7). A protonated molecular ion is observed at m/z=1348 as well as sodium-containing ions $(M+Na)^+$ at m/z=1370 and $(M+2Na-H)^+$ at m/z=1392. The ions at m/z=1268 and m/z=1047 are respectively attributed to the loss of $SO_3$ and an N-acetylglucosamine sulfate from $(M+H)^+$. The ions m/z=844, m/z=641 and m/z=438 are attributed to the glycosylium ions obtained by interglycoside cleavages. This spectrum indicates that Ac-NodRm-3:

(i) consists of a linear chain of five D-glucosamine derivatives;
(ii) possesses a diunsaturated N-acyl chain of 16 carbons and an O-acetate group on the nonreducing terminal glucosamine residue;
(iii) possesses a sulfate functional group on the reducing N-acetyl-D-glucosamine residue.

Incubation of the Ac-NodRm-3 compound in the presence of an exochitinase (extracted from *Streptococcus griseus*, Sigma) releases in particular an N-acetyl-D-glucosamine and N-acyl-O-acetyl-D-glucosamine dimer, which shows that the bonds between the first three N-acetyl-D-glucosamine residues are of the β-1,4 type. Digestion of Ac-NodRm-3 by an endochitinase (also extracted from *Streptococcus griseus*, Boeringer) leads to the formation of an N-acyl-O-acetyl-D-glucosamine showing that the bonding with the nonreducing terminal residue is also of the β-1,4 type.

Example 4 - Preparation of Nod factors from a *Rhizobium leguminosarum* biovar viciae culture medium A. Production of the Nod factors In European countries, the cultivation of protein-rich plants such as pea and field bean developed considerably during the last decade. The inventors therefore set out to study the production of the Nod factor by *Rhizobium leguminosarum* b.v. *viciae*, the symbiotic bacteria for these protein-rich plants.

The inventors introduced the plasmid plJ1089 into the *R. leguminosarum* strain 248 with the aim of causing an increase in the production of these signals. This plasmid, which is derived from the vector pLAFR1, contains the entire Nod region of *R. leguminosarum*, that is to say the operons nodD, nodABCIJ, nodFEL, nodMNT, nodO (Downie et al., EMBO J., 1983, 2, 947–952).

Strain 248 (plJ1089) is cultured in the same medium as *R. meliloti* but for inducing the transcription of the nod genes, a flavanone, naringenin, was used in place of luteolin. After inducing the nod genes, the culture supernatant exhibits a high activity of deformation of the root hairs of a suitable vetch species (*Vicia sativa* subsp. *nigra*). This activity is not detectible in the culture supernatants of an *R. leguminosarum* strain 248 which is mutated in the common genes nodABC.

B. Purification

The Nod compounds are extracted from the culture medium according to the procedure described in Example 1 (B.1.). The extract is freeze-dried and then chromatographed by reversed-phase HPLC according to the procedure described in Example 1 (B.1.2.). The Nod compounds are then purified on a Sep-Pak QMA cartridge (Waters Millipore) in the acetate form. The compounds are eluted with 5 ml of absolute ethanol.

C. Determination of the structure

The positive mode FABmass spectrum predominantly shows three protonated molecular ions at m/z=1067, m/z=1069 and m/z=1095, accompanied by their sodium-containing ions $(M+Na)^+$ at m/z=1089, m/z=1091 and m/z 1117 respectively. Decomposition, by MS/MS spectrometry, of the ion at m/z=1089 (m/z=1091 and m/z=1117 respectively) provides the fragment ions at m/z=868 (m/z=870 and m/z=896 respectively), m/z=665 (m/z=667 and m/z=693 respectively) and m/z=462 (m/z=464 and m/z=490 respectively). These ions are obtained by interglycoside rupture, with the successive loss of fragments α with a mass of 203, corresponding to an N-acetylglucosamine residue. These spectra show that the NodR1 compounds consist of a linear N-acetylhexosamine chain. The ions of m/z=462, 464 and 490 correspond to variously N-acylated O-acetylhexosamines.

Analysis of the fatty acids carried by the nonreducing terminal residue was carried out by GC/MS after saponification according to the procedure described in paragraph B.

2.2. This study made it possible to identify the following predominant fatty acids: $C_{16:0}$, $C_{15:1}$ and $C_{18:1}$.

As evident from the above, the invention is not in the least limited to the implementations, embodiments and applications which have just been described more explicitly; on the contrary, it embraces all the variants which may come to the mind of a specialist in this field without departing from the framework or the scope of the present invention.

We claim:

1. A purified lipo-oligosaccharide having formula I below:

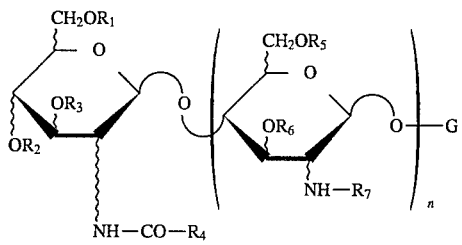

wherein G is selected from the group consisting of hexosamine, acetyl-substituted hexosamine, sulphated-substituted hexosamine, and ether-substituted hexosamine, $R_1, R_2, R_3, R_5, R_6$ and $R_7$, which are identical or different, are selected from the group consisting of H, $C_xH_yCO-$, and carbamyl, wherein x is an integer between 0 and 17, and y is an integer between 1 and 35, $R_4$ is selected from the group consisting of a mono-, di-, or tri-unsaturated aliphatic chain containing at least 12 carbon atoms, and n is an integer between 1 and 4.

2. The lipo-oligosaccharide of claim 1, wherein G represents a compound selected from the group consisting of N-acetyl-D-glucosamine 6-sulphate and N-acetyl-D-glucosamine.

3. The lipo-oligosaccharide of claim 1, having formula (II) below:

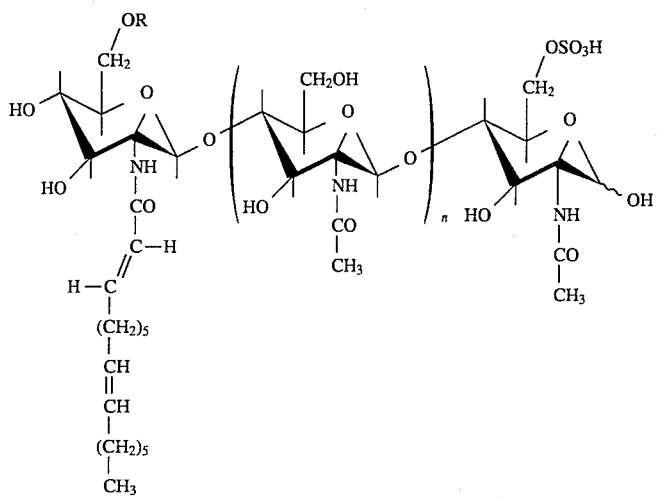

in which R is H or $CH_3CO-$ and n is equal to 2 or 3.

4. A composition for treating plants, comprising the lipo-oligosaccharide of claim 1, and an agriculturally suitable carrier.

5. The composition of claim 4, wherein the concentration of lipo-oligosaccharide is between $10^{-6}M$ and $10^{-14}M$.

6. A method for enhancing the capacity of a bacteria of the family Rhizobiacae to infect a host plant of the family Leguminoseae comprising administration to said plant of an amount effective to act as plant-specific symbiotic signal, of a lipo-oligosaccharide of claim 1.

7. The method of claim 6, wherein said lipo-oligosaccharide is at a concentration between $10^{-6}M$ and $10^{-14}M$.

8. A method of accelerating the formation of nodules on a host plant of the family Leguminoseae comprising administration to said plant of an amount effective to act as plant-specific symbiotic signal, of a lipo-oligosaccharide of claim 1.

9. The method of claim 8 wherein said lipo-oligosaccharide is at a concentration between $10^{-6}M$ and $10^{-14}M$.

10. A method of inducing the transcription of the symbiotic genes of Leguminoseae comprising administration to a Leguminoseae of an amount effective to act as plant-specific symbiotic signal, of a lipo-oligosaccharide of claim 1.

11. The method of claim 10 wherein said lipo-oligosaccharide is at a concentration between $10^{-6}M$ and $10^{-14}M$.

* * * * *